(12) United States Patent
Guo et al.

(10) Patent No.: US 10,076,589 B2
(45) Date of Patent: Sep. 18, 2018

(54) BIODEGRADABLE MEDICAL DEVICE HAVING AN ADJUSTABLE DEGRADATION RATE AND METHODS OF MAKING THE SAME

(71) Applicant: Board of Trustees of The University of Alabama, Tuscaloosa, AL (US)

(72) Inventors: Yuebin Guo, Tuscaloosa, AL (US); Michael Sealy, Hoover, AL (US); Meisam Salahshoor Pirsoltan, Tuscaloosa, AL (US)

(73) Assignee: The Board of Trustees of the University of Alabama, Tuscaloosa, AL (US)

( * ) Notice: Subject to any disclaimer, the term of this patent is extended or adjusted under 35 U.S.C. 154(b) by 418 days.

(21) Appl. No.: 14/790,487

(22) Filed: Jul. 2, 2015

(65) Prior Publication Data
US 2015/0314046 A1  Nov. 5, 2015

Related U.S. Application Data

(63) Continuation of application No. 13/966,671, filed on Aug. 14, 2013, now Pat. No. 9,084,843.
(Continued)

(51) Int. Cl.
*A61L 27/58*  (2006.01)
*A61B 17/86*  (2006.01)
(Continued)

(52) U.S. Cl.
CPC .............. *A61L 27/58* (2013.01); *A61B 17/68* (2013.01); *A61B 17/86* (2013.01); *A61B 17/866* (2013.01);
(Continued)

(58) Field of Classification Search
CPC ...... A61L 27/58; A61L 27/047; A61L 31/088; A61L 31/148; A61B 17/68; A61B 17/866;
(Continued)

(56) References Cited

U.S. PATENT DOCUMENTS 5,131,957 A  7/1992  Epstein et al.
5,569,018 A  10/1996  Mannava et al.
(Continued)

FOREIGN PATENT DOCUMENTS

WO  1997/041267  11/1997
WO  2006/108065  10/2006

OTHER PUBLICATIONS

Abbas, G., et al., "Corrosion Behavior of Laser-Melted Magnesium Alloys," Applied Surface Science, 247, 2005, pp. 347-353.
(Continued)

*Primary Examiner* — Jacob Cigna
*Assistant Examiner* — Lee A Holly
(74) *Attorney, Agent, or Firm* — Meunier Carlin & Curfman LLC

(57) ABSTRACT

Disclosed herein are biodegradable medical devices comprising biodegradable materials (e.g., magnesium-calcium alloys) having an adjustable rate of degradation that can be used in various applications including, but not limited to, drug delivery applications, cardiovascular applications, and orthopedic applications to make biodegradable and biocompatible devices. Also disclosed herein are methods of making biodegradable medical devices comprising biodegradable materials by using, for instance, hybrid dry cutting/hydrostatic burnishing.

17 Claims, 13 Drawing Sheets

Related U.S. Application Data

(60) Provisional application No. 61/682,890, filed on Aug. 14, 2012.

(51) Int. Cl.
| | |
|---|---|
| A61B 17/68 | (2006.01) |
| A61F 2/28 | (2006.01) |
| A61L 27/04 | (2006.01) |
| A61L 31/08 | (2006.01) |
| A61L 31/14 | (2006.01) |
| A61B 17/80 | (2006.01) |
| A61B 17/70 | (2006.01) |
| A61B 17/00 | (2006.01) |

(52) U.S. Cl.
CPC .............. *A61F 2/28* (2013.01); *A61L 27/047* (2013.01); *A61L 31/088* (2013.01); *A61L 31/148* (2013.01); *A61B 17/7002* (2013.01); *A61B 17/80* (2013.01); *A61B 2017/00004* (2013.01); *A61B 2017/00526* (2013.01); *A61F 2210/0004* (2013.01); *A61F 2240/001* (2013.01); *Y10T 29/47* (2015.01); *Y10T 428/12993* (2015.01)

(58) Field of Classification Search
CPC ............ A61B 17/86; A61B 2017/0004; A61B 17/7002; A61B 2017/00526; A61B 17/80; A61F 2/28; A61F 2240/001; A61F 2210/004; Y10T 29/47; Y10T 428/12993
See application file for complete search history.

(56) References Cited

U.S. PATENT DOCUMENTS

| | | | |
|---|---|---|---|
| 5,744,781 | A | 4/1998 | Yeaton |
| 6,197,133 | B1 | 3/2001 | Unternahrer et al. |
| 6,469,275 | B2 | 10/2002 | Dulaney et al. |
| 6,670,577 | B2 | 12/2003 | Stayer et al. |
| 6,752,593 | B2 | 6/2004 | Clauer et al. |
| 6,875,953 | B2 | 4/2005 | Clauer et al. |
| 6,911,100 | B1 | 6/2005 | Gibbs et al. |
| 6,923,877 | B1 | 8/2005 | Anderson |
| 7,762,113 | B2 | 7/2010 | Prevey, III |
| 8,033,152 | B2 | 10/2011 | Prevey, III |
| 8,293,031 | B2 | 10/2012 | Gerold et al. |
| 2005/0079088 | A1 | 4/2005 | Wirth et al. |
| 2006/0009857 | A1 | 1/2006 | Gibbs et al. |
| 2006/0229711 | A1* | 10/2006 | Yan .......................... A61F 2/02 623/1.38 |
| 2008/0015578 | A1 | 1/2008 | Erickson et al. |
| 2009/0043228 | A1 | 2/2009 | Northorp et al. |
| 2009/0081313 | A1* | 3/2009 | Aghion ................ A61L 27/047 424/641 |
| 2009/0131540 | A1 | 5/2009 | Hiromoto et al. |
| 2010/0075162 | A1 | 3/2010 | Yang et al. |
| 2010/0161053 | A1 | 6/2010 | Bayer |
| 2010/0249926 | A1 | 9/2010 | Kirschman et al. |
| 2010/0254848 | A1* | 10/2010 | Inoue ...................... C22C 23/02 420/408 |
| 2011/0054629 | A1 | 3/2011 | Seok et al. |
| 2011/0301694 | A1 | 12/2011 | Heublein et al. |
| 2013/0060326 | A1 | 3/2013 | Gerold |

OTHER PUBLICATIONS

Aksakal, B., et al., "Bioceramic Dipcoating on Ti-6Al-4V and 316L SS Implant Materials," Journal of Materials Science: Materials in Medicine, vol. 19, 2008, pp. 2097-2104.
Amelfarzad, H., et al., "In Body Corrosion Fatigue Failure of a Stainless Steel Orthopedic Implant With a Rare Collection of Different Damage Mechanisms," Eng. Fail. Anal., vol. 14, 2007, pp. 1205-1217.
Anderson, P., et al., "Microlubrication Effect by Laser-Textured Steel Surfaces," Wear, vol. 262, 2007, pp. 369-379.
Anscomb, A, "Orthopedic Biomaterials: World Market," New York, Kalorama Information, 2007.
Anurag, S., et al., "A New FEM Approach to Predict Residual Stress Profiles in Hard Tuning without Simulating Chip Formation," Trans. NAMRI/SME, vol. 38, 2010, pp. 33-40.
Anurag, S., et al., "A Predictive Model to Decouple the Contributions of Friction and Plastic Deformation to Machined Surface Temperatures and Residual Stress Patterns in Finish Dry Cutting," Frontiers of Mechanical Engineering, 2010, pp. 247-255.
Ataya, S., et al., "Quasi-Static Behavior of Mg-alloys With and Without Short Fiber Reinforcement," Theor. Appl. Fract. Mech., vol. 47, 2007, pp. 102-112.
Au, A. G., et al., "Contribution of Loading Conditions and Material Properties to Stress Shielding Near the Tibial Component of Total Knee Replacements," Journal of Biomechanics, vol. 40, 2007, pp. 1410-1416.
Bach, F.W., et al., "Influence of Cutting and Non-Cutting Processes on the Corrosion Behavior and the Mechanical Properties of Magnesium Alloys," Proceedings of the $7^{th}$ International Conference Mg Alloys & Their App., 2007, pp. 1076-1084.
Ballard, P., et al., "Residual Stresses Induced by Laser-Shocks," J. de Physique IV, C3, 1991, pp. 487-494.
Bammann, D.J., et al., "Failure in Ductile Materials Using Finite Element Methods," Jones N, Wierzbicki T (eds) Structural Crashworthiness and Failure, Elsevier, Essex, England, 1993, 54 pages.
Bammann, D.J., et al., "Modeling Large Deformation and Failure in Manufacturing Processes," Theoretical Applied Mechanics, Elsevier Science B.V., 1996, pp. 359-376.
Benli, S., et al., "Evaluation of Bone Plate with Low Stiffness Material in Terms of Stress Distribution," J. Biomech., vol. 41, 2008, pp. 3229-3235.
Bergen, G., et al., "Injury in the United States: 2007 Chart Book," National Center for Health Statistics, Hyattsville, MD, USA, 2008.
Berthe, L., et al., "Shock Waves From a Water-Confined Laser-Generated Plasma," Journal of Applied Physics, vol. 82, 1997, pp. 2826-2832.
Berthe, L., et al., "Wavelength Dependent Laser Shock-Wave Generation in the Water-Confinement Regime," Journal of Applied Physics, 1999, pp. 7552-7555.
Black, J.T., "Mechanics of Chip Formation," vol. 16, ASM Handbook, Machining, ASM International, Materials Park, OH, 2000, pp. 5-10.
Blatter, A., et al., "Lubricated Sliding Performance of Laser-Patterned Sapphire," Wear, 1999, pp. 226-230.
Bozdana, A.T., et al., "Comparative Experimental Study on Effects of Conventional and Ultrasonic Deep Cold Rolling Processes on Ti-6Al-4V," Mater. Sci. Tech., vol. 24, 2008, pp. 1378-1384.
Braisted, W. et al., "Finite Element Simulation of Laser Shock Peening," International Journal of Fatigue, vol. 21, 1999, pp. 719-724.
Brinksmeier, E., et al., "Cold Surface Hardening, CIRP Annals" Manuf. Tech., vol. 57, 2008, pp. 541-544.
Byrne, G., et al., "Advancing Cutting Technology," Annals of CIRP, 2003, pp. 483-507.
Caslaru, R., et al., "Fabrication and Characterization of Micro Dent Arrays by Laser Shock Peening on Ti-6Al-4V Surfaces," 2009, ASME.
Caslaru, R., et al., "Fabrication and Characterization of Micro Dent Array Produced by Laser Shock Peening on Aluminum Surfaces," North American Manufacturing Research Institution of the Society of Manufacturing Engineers, vol. 37, 2009, pp. 159-166.
Chen, H. et al., Systemical Characterization of Material Response to Microscale Laser Shock Peening, J. Manuf. Sci. Eng., 740, pp. 740-749 (2004).
Claes, L.E., Mechanical Characterization of Biodegradable Implants, Clinical Materials, 10, pp. 41-46 (1992).
Clauer, A. et al., Interaction of Laser-Induced Stress Waves With Metals, ASM Conference Applications of Laser in Material Processing, Washington DC, ASM Int., Material Park, OH 44073-0002, pp. 1-22 (1979).

(56) References Cited

OTHER PUBLICATIONS

Clauer, A., Laser Shock Peening for Fatigue Resistance, Proceedings of Surface Performance of Titanium, Gregory J.K., Rack H.J. and Eylon D. (eds), TMS, Warrendale, PA. The Metal Society of AIME, pp. 217-230 (1996).
Completo, A., et al., "Experimental Evaluation of Strain Shielding in Distal Femur in Revision," TKA Exp. Mech., vol. 48, 2008, pp. 817-824.
Completo, A., et al., "Strain Shielding in Proximal Tibia of Stemmed Knee Prosthesis: Experimental Study," Journal of Biomechanics, vol. 41, 2008, pp. 560-566.
Dane, C.B., et al., "High Laser Power for Peening of Metals Enabling Production Technology," Advanced Aerospace Materials and Process Conference 98, Tysons Corner, Virginia, 1998.
Danilenko, B.D., "Selecting the Initial Cutting Parameters in Machining Magnesium Alloys," Russ. Eng. Res. 29, 2009, pp. 316-318.
Davies, E.D.H., et al., "The Dynamic Compression Testing of Solids by the Method of Split Hopkinson Pressure Bar (SHPB)," J. Mech. Phys. Solids, vol. 11, 1963, pp. 155-179.
Denkena, B., et al., "Biocompatible Magnesium Alloys as Absorbable Implant Materials-Adjusted Surface and Subsurface Properties by Machining Processes," Annals of CIRP, vol. 56, No. 1, 2007, pp. 113-116.
Denkena, B., et al., "Degradable Implants Made of Magnesium Alloys," Proceedings of the 5th Euspen International Conference, Montpellier, France, 2005.
Denkena, B., et al., "Development of Combined Manufacturing Technologies for High-Strength Structure Components," Adv. Mater. Res., vol. 22, 2007, pp. 67-75.
Denkena, B., et al., "Safe Machining of Magnesium Parts by Cutting and Burnishing Operations," Proceedings of the $7^{th}$ International Conference Mg Alloys & Their App., 2004, pp. 895-901.
Devaux, D., et al., "Generation of Shock Waves by Laser-Induced Plasma in Confined Geometry," Journal of Applied Physics, vol. 74, 1993, pp. 2268-2273.
Ding, K., et al., "Three-Dimensional Dynamic Finite Element Analysis of Multiple Laser Shock Peening Processes," Surf. Eng., 2003, pp. 351-358.
Disegi, J. A., et al., "Effect of Low Plasticity Burnishing on the Fatigue Strength of Spinal Rods," Proc. of ASM MPMD (Materials & Processes for Medical Devices) Conference and Exposition, Minneapolis, MN, USA, 2009.
Drynda, A., et al., "Development and Biocompatibility of a Novel Corrodible Fluoride-Coated Magnesium-Calcium Alloy with Improved Degradation Kinetics and Adequate Mechanical Properties for Cardiovascular Applications," Journal of Biomedical Materials Research A, vol. 93, 2010, pp. 763-775.
Dumitru, G., "Laser Microstructuring of Steel Surfaces for Tribological Applications," App. Physics A, vol. 70, 2000, pp. 485-487.
El-Magd, E., et al., "Adiabatic Flow Curves of Metallic Materials at High Strain Rates," Mat. Wiss. U. Werkst., vol. 27, 1996, pp. 408-413.
El-Magd, E., et al. "Characterization, Modeling and Simulation of Deformation and Fracture Behavior of the Light-Weight Wrought Alloys Under High Strain Rate Loading," Int. J. Impact Eng., vol. 32, 2006, pp. 741-758.
El-Magd, E., et al, "Compression Test on Magnesium Alloy MgAl8Zn at High Strain Rates and Temperature in Magnesium Alloys and Their Applications," Kainer, K.U., Ed., Wiley-VCH Verlag GmbH & Co., Hoboken, NJ, USA, 2000, pp. 324-329.
El-Magd, E., et al. "Influence of Strain Rate and Temperature on the Compressive Ductility of Al, Mg, Ti alloys," J. Phys. Paris, vol. 110, 2003, pp. 15-20.
El-Magd, E., et al., "Influence of Strain Rate and Temperature on Deformation and Fracture Behavior of Magnesium Alloy MgAl8Zn: Tests and Numerical Simulations," In Proceedings of the 6th International Conference on Magnesium Alloys and Their Applications, Kainer, K.U., Ed.; Wiley-VCH Verlag GmbH & Co.: Hoboken, NJ, USA, 2004, pp. 402-408.

Essa, Y.E., et al., "Effects of the Strain Rate and Temperature on the Mechanical Behavior of a Mg-5%Zn Alloy Reinforced with SiC Particles," J. Mater. Process. Tech., 2003, pp. 856-859.
Etison, I., "Laser Surface Textured Hydrostatic Mechanical Seal," Sealing Tech., 2003, pp. 6-10.
Etison, I., "State of Art in Laser Surface Texturing," J. Tribology, vol. 127, 2005, pp. 248-253.
Fabbro, R., et al., "Physical Study of Laser-Produced Plasma in Confined Geometry," Journal of Applied Physics, vol. 68, 1990, pp. 775-784.
Fairand, B.P., et al., "Effect of Water and Paint Coatings on the Magnitude of Laser-Generated Shock Waves," Optics Communications, 1976, pp. 588-591.
Fairand, B.P., et al., "Laser Shock-Induced Microstructure and Mechanical Property Changes in 7075 Aluminum," Journal of Applied Physics, vol. 43, 1972, pp. 3893-3895.
Fan, Y., "Microscale Laser Peen Forming of Single Crystal: Dynamic Deformation and Anisotropy," Trans. SME/NAMRI, vol. 35, 2007, pp. 383-390.
Fan, Y., "Wave-Solid Interactions in Laser-Shocked-Induced Deformation Processes," Journal of Applied Physics, vol. 98, 2005.
Fang, F.Z., et al., "An Experimental Study of Micromachining Step Mirrors for Laser-Diode Beam Shaping," Journal of Micromechanics and Microengineering, vol. 16, 2006, pp. 214-218.
Fang, F.Z., et al., "Burr Formation in Fly-Cutting," STR, vol. 22, 2003, pp. 1-9.
Fang, F.Z., et al., "Mean Flank Temperature in High Speed Cutting of Magnesium Alloy," Journal of Materials Processing Technology, vol. 167, 2005, pp. 119-123.
Feser, K., et al., "Effects of Degradable Mg—Ca Alloys on Dendritic Cell Function," Journal of Biomaterials Applications, vol. 25, 2011, pp. 685-697.
Friedrich, C.R., "Micromechanical Machining of High Aspect Ratio Prototypes," Microsystem Tech., vol. 8, 2002, pp. 343-350.
Friemuth, T., et al., Machining of Magnesium Workpieces: Advanced Engineering Material 1999, pp. 183-186.
Fu, C.H., et al., "Austenite-Martensite Phase Transformation of Biomedical Nitinol by Ball Burnishing," Journal of Materials Processing Technology, vol. 214, No. 12, 2014, pp. 3122-3130.
Gama, B.A., et al., "Hopkinson Bar Experimental Technique: A Critical Review," Appl. Mech. Rev., vol. 57, 2004, pp. 223-250.
Gefen, A., "Computational Simulations of Stress Shielding and Bone Resorption Around Existing and Computer-Designed Orthopaedic Screws," Medical & Biological Engineering & Computing, vol. 40, 2002, pp. 311-322.
Geiger, M., et al., "Excimer Laser Micro Texturing of Cold Forging Tool Surfaces-Influence on Tool Life," Ann. CIRP 2002, pp. 231-234.
Gill, C.M., et al., "Shakedown of Deep Cold Rolling Residual Stresses in Titanium Alloys," J. Phys. D: Appl. Phys., vol. 41, 2008, 5 pages.
"The Future of Orthopedic Implants, Analysis and Forecasts to 2016—Joint Reconstructive and Spinal Implants Creating Growth Opportunities," Global Business Intelligence Research Report, 2010.
Gray III, G.T., "Classic Split-Hopkinson Pressure Bar Testing," ASM Handbook, vol. 8, Mechanical Testing and Evaluation, ASM International, Materials Park OH, 2000, pp. 462-476.
Grimm, M.J., "Biomedical Engineering Design Handbook: Orthopedic Biomaterials," $2^{nd}$ Ed., M. Kutz, Ed., McGraw-Hill, 2009.
Gu, X.N., et al., "A Study on Alkaline Heat Treated Mg—Ca Alloy for the Control of the Biocorrosion Rate," Acta Biomater, vol. 5, 2009, pp. 2790-2799.
Gu, X.N., et al., "Influence of Artificial Biological Fluid Composition on the Biocorrosion of Potential Orthopedic Mg—Ca, AZ31, AZ91 Alloys," Biomed. Mater., vol. 4, 2009.
Guo, Y., et al., "Characterization and Modification of Surface Topography by Sequential Laser Peening Biodegradable Magnesium-Calcium Alloy," Proc. of ASME 5th Frontiers in Biomed. Devices Conf. and Exhibition, 2010.
Guo, Y., et al., "3D FEA Modeling of Hard Turning," J. Manuf. Sci. Eng., vol. 124, 2002, pp. 189-199.

(56) References Cited

OTHER PUBLICATIONS

Guo, Y., et al., "An Internal State Variable Plasticity Based Approach to Determine Dynamic Loading History Effects in Manufacturing Processes," Int. J. of Mechanical Sciences, vol. 47, 2005, pp. 1423-1441.
Guo, Y., et al. "Bio-Performance Improvement of Novel Biodegradable Mg—Ca Implants by Hybrid Dry Cutting-Burnishing," Professor and Director Center for Surface Integrity and Functionality, The Univ. of Alabama, PowerPoint presentation, 2012, 16 pages.
Guo, Y., et al., "Characterization of Mechanical Property and Microstructure of Biomedical Magnesium Alloy," Proc. of ASM MPMD (Materials & Processes for Medical Devices) Conference and Exposition, Minneapolis, MN, 2009.
Guo, Y., "Hybrid Dry Cutting—Finish Burnishing of Novel Biodegradable Magnesium-Calcium Implants for Superior Corrosion Performance," 2010.
Guo, Y., et al., "Process Mechanics and Surface Integrity by High-Speed Dry Milling of Biodegradable Magnesium-Calcium Implant Alloys," CIRP Ann. Manuf. Tech., vol. 59, 2010, pp. 151-154.
Guo, Y., et al., "Significant Improvement of Corrosion Resistance of Biodegradable Metallic Implants Processed by Laser Shock Peening," CIRP Annals—Manufacturing Technology, 2012, 4 pages.
Guo, Y., et al., Sustainable High Speed Dry Cutting of Magnesium Alloys, Materials Science Forum, vol. 723, 2012, pp. 3-13.
Guo, Y., et al., "The Basic Relationship Between Machining Induced Residual Stress Profiles and Fatigue Life," ASME International Conference on Manufacturing Science and Engineering, Evanston, IL, USA, 2008.
Guo, Y., et al., "The Basic Relationships Between Residual Stress, White Layer, and Fatigue Life of Hard Turned and Ground Surfaces in Rolling Contact," CIRP J. Manuf. Sci. Tech., 2010, pp. 129-134.
Hallum, D.L., "Magnesium: Lightweight, Easy to Machine," Am. Mach., vol. 139, 1995, pp. 48-51.
Hassel, et al., "Influence of Alloy Composition on the Mechanical and Electrochemical Properties of Binary Mg—Ca Alloys and Its Corrosion Behavior in Solutions at Different Chloride Concentrations in Magnesium," Proceedings of 7th International Conference on Magnesium Alloys and Their Applications; Kainer, K.U., Ed.; Wiley-VCH Verlag GmbH & Co., 2007, pp. 789-795.
Hassel, T., et al., "Production and Properties of Small Tubes Made From (MgCa0.8) For Application as Stent in Biomedical Science," In Proceedings of the 7th International Conference on Magnesium Alloys and Their Applications, Kainer, K.U., Ed.; Wiley-VCH Verlag GmbH & Co.: Hoboken, NJ, USA, 2007, pp. 432-437.
Hench, L., et al., "Third Generation Biomedical Materials," Science, vol. 295, 2002, pp. 1014-1017.
Heublein, B., et al., "Biocorrosion of Magnesium Alloys: A New Principle in Cardiovascular Implant Technology," Heart, vol. 89, 2003, pp. 651-656.
Ilich, J.Z., et al., "Nutrition in Bone Health Revisited: A Story Beyond Calcium," Journal of the American College of Nutrition, vol. 19, 2000, pp. 715-737.
Iordanova, I., et al., "Changes of Microstructure and Mechanical Properties of Cold-Rolled Low Carbon-Steel Due to Its Surface Treatment by Nd: glass Pulsed Laser," Surf. Coating Tech., vol. 153, 2002, pp. 267-275.
Isaksson, H., et al., "Mathematical Modeling of Stress Shielding With Bioresorbable Materials for Internal Fracture Fixation," In Proceedings of the IEEE 29th Annual Bioengineering Conference, Newark, NJ, USA, 2007, pp. 1041-1042.
Jayaraman, N., et al., "Mitigation of Fatigue and Pre-Cracking Damage in Aircraft Structures Through Low Plasticity Burnishing," In Proceedings of the USAF Aircraft Structural Integrity Program (ASIP), Palm Springs, CA, 2007.
Juijerm, P., et al., "Effective Boundary of Deep-Rolling Treatment and Its Correlation With Residual Stress Stability of Al—Mg—Mn and Al—Mg—Si—Cu Alloys," Scripta Materialia, vol. 56, 2007, pp. 745-748.

Kainer, K.U., "Deformation Behavior of AZ Alloys at High Strain Rates in Magnesium Alloys and Their Applications," Mordike, K.U., Eds.; Werkstoff-Informationsgesellschaft: Frankfurt, Germany, 1998, pp. 369-374.
Kanchanomai, C. et al., "Fatigue Failure of an Orthopedic Implant—A Locking Compression Plate," Eng. Fail. Anal., vol. 15, 2008, pp. 521-530.
Kannan, M., "Alloys in Modified Simulated Body Fluid, Biomaterials," vol. 29, 2008, pp. 2306-2314.
Kieswetter, K.B., et al., "In vitro Degradation and Mechanical Integrity of Calcium Containing Magnesium: The Role of Implant Surface Characteristics in the Healing of Bone," Critical Review of Oral and Biol. Med., vol. 7, No. 4, 1996, pp. 329-345.
Kirkland, N.T., et al., "In-Vitro Dissolution of Magnesium-Calcium Binary Alloys: Clarifying the Unique Role of Calcium Additions in Bioresorbable Magnesium Implant Alloys," Journal of Biomedical Materials Research, Part B: Applied Biomaterials, vol. 95, 2010, pp. 91-100.
Krause, A., et al., "Degradation Behavior and Mechanical Properties of Magnesium Implants in Rabbit Tibiae," Journal of Materials Science, vol. 45, 2010, pp. 624-632.
Kulkani, K., et al., "Surface Micro/Nanostructuring of Cutting Tool Materials by Femtosecond Laser," Trans. SME/NAMRI, vol. 32, 2004, pp. 25-32.
Lathrop, J.F., "BFIT—A Program to Analyze and Fit the BCJ Model Parameters to Experimental Data," Sandia Labs Report, 1996, pp. 97-8218.
Li, M., et al., "Corrosion Behavior in SBF for Titania Coatings on Mg—Ca Alloy," J. Mater. Sci., vol. 46, 2011, pp. 2365-2369.
Li, W., et al., "Analysis of Variance Based Predictive Model for Surface Roughness in End Milling of IN 718 NAMRC41-1609, MSEC 2013 NAMRC 41," ASME International Manufacturing Science and Engineering Conference, SME North American Manufacturing Research Conference, Jun. 10-14, 2013, Madison Wisconsin, Abstract.
Li, Z., et al., "The Development of Binary Mg—Ca Alloys for Use as Biodegradable Materials Within Bone," Biomaterials, vol. 29, 2008, pp. 1329-1344.
Liu, C., et al., "Influence of Heat Treatment on Degradation Behavior of Bio-Degradable Die-Cast AZ63 Magnesium Alloy in Simulated Body Fluid," Material of Sci. & Eng., 2007, pp. 350-357.
Liu, C., et al., "In Vitro Corrosion Degradation Behavior of Mg—Ca Alloy in the Presence of Albumin," Corros. Sci., vol. 52, 2010, pp. 3341-3347.
Lopez, L.N., et al., "The Effect of Ball Burnishing in Heat Treated Steel and Inconel 718 Milled Surfaces," Int. J. Adv. Manuf. Tech., vol. 32, 2007, pp. 958-968.
Majzoobi, G.H., et al., "The Effects of Deep Rolling and Shot Peening on Fretting Resistance of Aluminum-7075-T6," Mater. Sci. Eng. A, vol. 516, 2009, pp. 235-247.
Masse, J.E., et al., "Laser Generation of Stress Waves in Metal, Surface and Coatings Technology," vol. 70, 1995, pp. 179-191.
Merchant, "Mechanics of the Metal Cutting Process I: Orthogonal Cutting and a Type 2 Chip," J. Appl. Phys., vol. 16, 1945, pp. 267-275.
Miller, D.L., et al., "A Review of Locking Compression Plate Biomechanics and Their Advantages as Internal Fixators in Fracture Healing," Clinical Biomechanical, vol. 22, 2007, pp. 1049-1062.
Mondal, A., et al., "Effect of Laser Surface Treatment on Corrosion and Wear Resistance of ACM720 Mg Alloy," Surface Coatings and Technology, vol. 202, 2008, pp. 3187-3198.
Montross, C.S., "Laser-Induced Shock Wave Generation and Shock Wave Enhancement in Basalt," Rock Mechanics and Mining Sciences, vol. 36, 1999, pp. 849-855.
Nagels, J., et al., "Stress Shielding and Bone Resorption in Shoulder Arthroplasty," Journal of Shoulder and Elbow Surgery, vol. 12, 2003, pp. 35-39.
Nakatsuji, T., et al., "The Tribological Effect of Electrolytically Produced Micro-Pools and Phosphoric Compounds on Medium Carbon Steel Surfaces in Rolling-Sliding Contact," Tribology Transactions, vol. 44, 2001, pp. 173-178.
Nakatsuji, T., et al., "The Tribological Effect of Mechanically Produced Micro-Dents by a Micro-Dents by a Micro Diamond

(56) References Cited

OTHER PUBLICATIONS

Pyramid on Medium Carbon Steel Surfaces in Rolling-Sliding Contact," Mechanica, vol. 36, 2001, pp. 663-674.
Nalla, R., et al., "On the Influence of Mechanical Surface Treatments—Deep Rolling and Laser Shock Peening—On The fatigue Behavior of Ti-64Al-4V at Ambient and Elevated Temperatures," Mater. Sci. Eng., 2003, pp. 216-230.
National Statistics for Outcomes by Patient and Hospital Characteristics for CCS Principal Diagnosis (2008), Retrieved Sep. 11, 2010, from HCUPnet://www.hcupnet.ahrq.gov.
Navarro, M., et al., "Biomaterials in Orthopaedics," J.R. Soc. Interface, vol. 5, 2008, pp. 1137-1158.
Nikitin, I., et al., "Comparison of the Fatigue Behavior and Residual Stress Stability of Laser-Shock Peened and Deep Rolled Austenitic Stainless Steel AISI 304 in the Temperature Range 25-600 C," Mater. Sci. Eng. A, vol. 465, 2007, pp. 176-182.
Nikitin, I., et al., "Correlation Between Residual Stress and Plastic Strain Amplitude During Low Cycle Fatigue of Mechanically Surface Treated Austenitic Stainless Steel AISI 304 and Ferritic-Pearlitic Steel SAE 1045," Mater. Sci. Eng.: A, vol. 491, 2008, pp. 297-303.
Nikitin, I., et al., "Residual Stress Relaxation of Deep-Rolled Austenitic Steel," Scr. Mater., vol. 58, 2008, pp. 239-242.
NSF CMMI/MPM, Grant No. 0555269 (request and published abstract).
NSF CMMI/MPM, Grant No. 1000706 (grant request).
Osternig, L., BNSTRUC University of Oregon, (Jan. 14, 1997), Retrieved Dec. 9, 2010, from Index of /~louiso: http://darkwing.uoregon.edu/~louiso/.
Pedersen, W., et al., "Facing SiCp/Mg Metal Matric Composites with Carbide Tools," J. Mater. Process. Technol., vol. 172, 2006, pp. 417-423.
Pettersson, U., et al., "Influence of Surface Texture on Boundary Lubricated Sliding Contacts," Tri. Int., vol. 36, 2003, pp. 857-864.
Peyre, P., et al., "Laser Shock Processing of Aluminum Alloys—Application to High Cycle Fatigue Behavior," Mater Sci. Eng.: A, 1996, pp. 102-113.
Prevey, P.S., et al., "Case Studies of Fatigue Life Improvement Using Low Plasticity Burnishing in Gas Turbine Engine Applications" J. Eng. Gas Turbines and Power, vol. 128, 2006, pp. 865-872.
Prevey, P.S. et al., "Controlled Plasticity Burnishing to Improve the Performance of Friction Stir Processed Ni—Al Bronze," Proceedings Thermec 2006, Vancouver, Canada, 2006.
Prevey, P.S., et al., "The Influence of Surface Enhancement by Low Plasticity Burnishing on the Corrosion Fatigue Performance of AA7075-T6," Int. J. Fatigue, vol. 26, 2004, pp. 975-982.
Rad, H.R.B., et al., "Microstructure Analysis and Corrosion Behavior of Biodegradable Mg—Ca Implant Alloys," Materials Design, vol. 33, 2012, pp. 88-97.
Rao, D.S., et al., "U.N. Investigation on the Effect of Ball Burnishing Parameters on Surface Hardness and Wear Resistance of HSLA Dual-Phase Steels," Mater. Manuf. Process., vol. 23, 2008, pp. 295-302.
Romano, V., "Laser Surface Microstructuring to Improve Tribological Systems," Proc. SPIE, 2003, pp. 199-211.
Roseler, B., et al., "Current-Potential Correlated Noise Measurement (CorrELNoise): A New Technique for the Evaluation of Electrochemical Noise Analysis," Mater. Corros., vol. 52, 2001, pp. 413-417.
Ruschau, J., et al., "Fatigue Crack Nucleation and Growth Rate Behavior of Laser Shock Peened Titanium," Int. J. Fatigue, vol. 21, 1999, pp. 199-209.
Salahshoor, M., et al., "Biodegradable Orthopedic Magnesium-Calcium (MgCa) Alloys, Processing, and Corrosion Performance," Materials, vol. 5, No. 1, 2012, pp. 135-155.
Salahshoor, M., et al., "Continuous Model for Analytical Prediction of Chatter in Milling," Int. J. Mach Tools Manuf., vol. 49, 2009, pp. 1136-1143.
Salahshoor, M., et al., "Cutting Mechanics in High Speed Dry Machining of Biomedical Magnesium-Calcium Alloy Using Internal State Variable Plasticity Model," Intl J. Machine Tools & Manufacture, vol. 51, 2011, pp. 579-590.
Salahshoor M., et al., "Machining Characteristics of High Speed Dry Milling of Biodegradable Magnesium-Calcium Alloy," Proceedings of the 2010 ASME Int'l Mfg Sci. & Eng'g Conference MSEC2010-34310, Erie, PA, USA, 2010, 8 pages.
Salahshoor, M., et al., "Numerical Modeling and Simulation of High Speed Machining Biomedical Magnesium Calcium Alloy," Proc. of ASM MPMD (Materials & Processes for Medical Devices) Conf. and Expo. Minneapolis, MN, 2009.
Salahshoor, M., et al., "Process Mechanics in Ball Burnishing Biomedical Magnesium-Calcium Alloy," Intl J. Advanced Mfg Tech., vol. 64, 2012, pp. 133-144.
Salahshoor, M., et al., "Process-Property-Performance Paradigm in Hybrid Manufacturing of Biodegradable Metallic Materials," MIME Faculty Candidate Seminar, 2013.
Salahshoor, M., et al., "Surface Integrity of Biodegradable Magnesium-Calcium Orthopedic Implant by Burnishing," J. Mechanical Behavior of Biomedical Materials, vol. 4, 2011, pp. 1888-1904.
Salahshoor M., et al., "Surface Integrity of Biodegradable Orthopedic Magnesium-Calcium Alloy by High-Speed Dry Face Milling," Prod. Eng. Res. Devel. (WGP), vol. 5, 2011, pp. 641-650.
Sanz, C., et al., "Efficient and Ecological Machining of Magnesium Hybrid Parts," in: Proceedings of the Seventh International Conference on Mg Alloys and their Applications, 2007, pp. 916-921.
Scheel, J.E., et al., "Safe Life Conversion of Aircraft Aluminum Structures Via Low Plasticity Burnishing for Mitigation of Corrosion Related Failures," Dept. of Defense Corrosion Conf., Gaylord National, Washington DC, In Proceedings of the Preliminary Program for 2009 DoD Corrosion Conference, Washington, DC, USA, 2009.
Schuh A., et al, "Deep Rolling of Titanium Rods for Application in Modular Total Hip Arthroplasty" J. Biomed. Mater. Res. Part B: Applied Biomaterials, 2006.
Schwerin, R., et al., "Experiences with the Machining of Magnesium," In: Proceedings of the Seventh International Conference on Mg Alloys and Their Applications, 2007, pp. 922-925.
Schmidt, J. et al., "Machining of Magnesium Castings," Aluminum, 1998, pp. 412-417.
Scott, D., "OEM Contract Manufacturing in Medical Devices," Total Contract Manufacturing Markets vols. I-III, New York: Kalorama Information, 2007.
Sealy, M.P., et al., "Characterization and Modification of Surface Integrity by Laser Peening Biodegradable Magnesium-Calcium Alloys," Proc. of Soc. for Biomaterials 34th Annual Meeting and Exhibition, 2010.
Sealy, M.P., et al., "Fabrication and Characterization of Porous Surface Microstructure of Biodegradable Magnesium-Calcium Implants by Laser Shock Peening and Finite Element Simulation," The $2^{nd}$ International Conference on Laser Peening, San Francisco, CA, 2010.
Sealy, M.P., et al., "Fabrication and Characterization of Surface Texture for Bone Ingrowth by Sequential Laser Peening Biodegradable Orthopedic Magnesium-Calcium Implants," Journal of Medical Devices, vol. 5, Issue 1, ASME, 2011.
Sealy, M.P., et al., "Fabrication and Finite Element Analysis of Micro Dents Using µ-Laser Shock Peening," Northwestern University, 2008 ASME International Conference on Manufacturing Science and Engineering, 2008.
Sealy, M.P., et al., "Fabrication and Finite Element Simulation of Sequential Laser Shock Peening of Biodegradable Mg—Ca Implants," Proceeding of the ASME 2009 International Manufacturing Science and Engineering Conference, West Lafayette, IN, USA, 2009, 8 pgs.
Sealy, M.P. et al.,"Fabrication and Finite Element Simulation of µ-laser Shock Peening for Micro Dents,"Int. J. Comp. Methods in Eng. Sci. & Mech., vol. 10, 2008, pp. 149-157.
Sealy, M.P., "Fabrication and Finite Element Simulation of Sequential Laser Shock Peening of Biodegradable Mg—Ca," Dept. of Mechanical Engineering Center for Surface Science and Engineering, Second International Conference on Laser Peening, San Francisco, CA, PowerPoint presentation, 2010, 26 pages.
Sealy, M.P., et al., "Fabrication and Finite Element Simulation of Sequential Laser Shock Peening of Biodegradable Mg—Ca Implants,"

(56) References Cited

OTHER PUBLICATIONS

Proceeding of the ASME 2009 International Manufacturing Science and Engineering Conference, PowerPoint presentation, 2009, 45 pages.

Sealy, M.P., "Finite Element Analysis to Improve Dimentional Accuracy in Nanomanufacturing V-Shape Microgrooves," University of Alabama, Center for Surface Integrity and Functionality, Tuscaloosa, AL, 2010, 8 pages.

Sealy, M.P., et al., "Laser Direct-Write Micro Dents Using Laser Shock Peening: Experimental Study and Numerical Simulations," ASME, Google Scholar Citations, 2008.

Sealy, M.P., "Orthopedic Use of Absorbable Mg—Ca Implants Processed by Laser Shock Peening," Dept. of Mechanical Engineering Center for Surface Integrity and Functionality, Biomedical Product Development, PowerPoint presentation, 2010, 5 pages.

Sealy, M.P., et al., "Surface Integrity and Process Mechanics of Laser Shock Peening of Novel Biodegradable Magnesium-Calcium (Mg—Ca) Alloy," Journal of the Mechanical Behavior of Biomedical Materials, vol. 3, Issue 7, 2010, pp. 488-496.

Seemikeri, C.Y., et al., "Low Plasticity Burnishing: An Innovative Manufacturing Method for Biomedical Applications,"J. Manuf. Sci. Eng., 2008, pp. 021008-021008.

Seemikeri, C.Y., et al., "Investigations on Surface Integrity of AISI 1045 Using LPB tool," Tribol. Int., vol. 41, 2008, pp. 724-734.

Sequera, et al., "Uncertainty Analysis of Tool Wear and Surface Roughness," MSEC 2013, NAMRC 41, ASME International Manufacturing Science and Engineering Conference, Madison Wisconsin, 2013.

Shi, J. F., et al., "A Dynamic Model of Simulating Stress Distribution in the Distal Femur After Total Knee Replacement," Proceedings of the I MECH E Part H, Journal of Engineering in Medicine, vol. 221, 2007, pp. 903-912.

Smith, J., "Advanced Polymers for Medical Applications," MarketResearch.com, New York: Kalorama Information, 2002.

Song, G., et al., "A Possible Biodegradable Magnesium Implant Material," Adv. Eng. Mater, vol. 9, 2007, pp. 298-302.

Song, G., "Control of Biodegradation of Biocompatible Magnesium Alloys," Corrosion Science, vol. 49, 2007, pp. 1696-1701.

Staiger, M.P. et al., "Magnesium and its Alloys as Orthopedic Biomaterials: A review," Biomaterials, vol. 27, 2006, pp. 1728-1734.

Sun, J., et al., "Surface Integrity and End Milled TI-6AL-4V Using the TIALN Coated Tool," ASME MESC and JSME ICM&P, Evanston, IL, USA, Northwestern University, 2008.

The Columbia Encyclopedia, Sixth Ed., bone, Retrieved Oct. 3, 2010, from Encyclopedia.com:http://www.encyclopedia.com, 2008.

Thomann, M., et al., "Comparison of the Resorbable Magnesium Alloys LAE442 and MgCa0.8 Concerning Their Mechanical Properties, Their Progress of Degradation and the Bone-Implant Contact After 12 Months Implantation Duration in a Rabbit Model," Materialwiss. Werkst., vol. 40, 2009, pp. 82-87.

Thomann, M., et al., "Influence of a Magnesium-Fluoride Coating of Magnesium-Based Implants (MgCa0.8) on Degradation in a Rabbit Model," J. Biomed. Mater. Rer. A, vol. 93, 2010, pp. 1609-1619.

Tomac, N., et al., "Formation of Flank Build-up in Cutting Magnesium Alloys," Annals of CIRP, vol. 40, No. 1, 1991, pp. 79-82.

Tönshoff, H.K., et al., "Improving the Characteristics of Magnesium Workpieces by Burnishing Operations, In Magnesium Alloys and Their Applications," Wiley-VCH: Hoboken, NJ, USA, 2000, pp. 406-411.

Tönshoff, H.K., et al., "Machining of Light Metals," Mat.-wiss. u. Werkstofftech 30, 1999, pp. 401-417.

Tönshoff, H.K., et al., "The Influence of Tool Coatings in Machining of Magnesium," Surface & Coatings Technology, 1997, pp. 94-95 and 610-616.

Trent, E.M., et al., Metal Cutting, 4th ed., Butterworth-Heinemann, Boston, 2000, pp. 12-30.

Triantafyllidis, G.K, et al., "Premature Fracture of a Stainless Steel 316L Orthopedic Plate Implant by Alternative Episodes of Fatigue and Cleavage Decoherence," Eng. Fail. Anal., 14, 2007, pp. 1346-1350.

Tsuji, N., et al. "Effect of Combined Plasma-Carburizing and Deep Rolling on Notch Fatigue Property of Ti-6Al-4V Alloy," Mater. Sci. Eng. A, vol. 499, 2009, pp. 482-488.

Tsuji, N., et al., "Evaluation of Surface-Modified Ti-6Al-4V Alloy by Combination of Plasma-Carburizing and Deep-Rolling," Mater. Sci. Eng. A, vol. 488, 2008, pp. 139-145.

Videm, M., et al., "Metallurgical Considerations for Machining Magnesium Alloys," SAE Transactions, vol. 103, 1994, pp. 213-220.

Von Der Höh, N., et al., "Influence of Different Surface Machining Treatments of Magnesium-Based Resorbable Implants on the Degradation Behavior in Rabbits," Advanced Engineering Materials, vol. 11, 2009, pp. B47-B54.

Waikar, R., et al, "A Comparative Study on the Effect of Surface Topography by Hard Turning Versus Grinding on Frictional Performance at Dry and Lubricated Sliding Contact," MSEC_ICMP2008-72232, MSEC 2008 ASME International Conference on Manufacturing Science and Engineering, $3^{rd}$ JSME/ASME International Conference on Materials and Processing, ICM&P, 2008, Northwestern University, Evanston, IL, USA, 2008.

Waikar, R.A., et al., "An Experimental Study on the Effect of Machining Induced White Layer on Frictional and Wear Performance at Dry and Lubricated Sliding Contact," Tribology Trans., 2010, pp. 127-136.

Waikar, R., et al., "Fabrication and Characterization of Bulk Nanocrystalline Layer by Shot Peening (SP)," $11^{th}$ International Conference on Shot Peening, South Bend, IN, USA, 2011.

Waikar, R.A., et al., "Fabrication and Characterization of Bulk Nanostructured Materials of Steel of Aluminum Alloys by Shot Peening," Trans NAMRI/SME, vol. 38, 2010, pp. 419-425.

Wakuda, M., et al., "Effect of Surface Texturing on Friction Reduction Between Ceramic and Steel Materials Under Lubricated Sliding Contact," Wear, vol. 254, 2003, pp. 356-363.

Wang, H., et al., "Bio Corrosion of a Magnesium Alloy with Different Processing Histories," Mater. Lett., 2007, pp. 2476-2479.

Wang, H., et al., "The Effect of Pre-Processing and Grain Structure on the Bio Corrosion and Fatigue Resistance of Magnesium Alloy AZ31," Adv. Eng. Mater. vol. 9, 2007, pp. 967-972.

Warren, A.W., et al., "A Numerical Simulation of Massive Parallel Laser Shock Peening," Proc. of ASME International Mechanical Engineering Congress & Exposition, Orlando, FL, 2005.

Warren, A. W., "Characteristics of Residual Stress Profiles in Hard Turned Versus Ground Surfaces With and Without a White Layer," MSEC_ICMP2008-72230, MSEC, 2008 ASME International Conference on Manufacturing Science and Engineering, $3^{rd}$ JSME/ASME International Conference on Materials and Processing, 2008, Northwestern University, Evanston, IL, USA, 2008.

Warren, A.W., et al., "FEA Modeling and Analysis of 3d Pressure and Mechanical Behavior at High Strain Rate in Micro Laser Peening," Trans. NAMRI/SME, vol. 35, pp. 409-416, 2007.

Warren, A.W., et al., "Massive Parallel Micro Laser Shock Peening: Simulation, Validation, and Analysis," International Journal of Fatigue, vol. 30, 2008, pp. 188-197.

White, R.M., "Elastic Wave Generation by Electron Bombardment of Electromagnetic Wave Absorption," J. App. Physics, vol. 34, 1963, pp. 2123-2127.

Witte, F., et al., "In Vivo Corrosion of Four Magnesium Alloys and the Associated Bone Response," Biomaterials, vol. 26, 2005, pp. 3557-3563.

Witte, F., et al., "Magnesium-Hydroxyapatite Composites as an Approach to Degradable Biomaterials," In Proceedings of the 7th International Conference on Magnesium Alloys and Their Applications, Kainer, K.U., Ed.; Wiley-VCH Verlag GmbH & Co.: Hoboken, NJ, USA, 2007, pp. 958-964.

Wu, B., et al., "A Self-Closed Thermal Model for Laser Shock Peening Under the Water Confinement Regime Configuration and Comparisons to Experiments," Journal of Applied Physics, vol. 97, 2005, pp. 1-12.

(56) References Cited

OTHER PUBLICATIONS

Wu, G., et al., "The Effect of Ca and Rare Earth Elements on the Microstructure, Mechanical Properties and Corrosion Behavior of AZ91D," Material Science and Engineering, vol. A408, 2005, pp. 255-263.
Yang, J., et al., "Laser Shock Peening on Fatigue Behavior of 2024-T3 Al Alloy With Fastener Holes and Stopholes," Mater. Sci. Eng., vol. A298, 2000, pp. 296-305.
Zhang, C.Y., et al., "Comparison of Calcium Phosphate Coatings on Mg—Al and Mg—Ca Alloys and Their Corrosion Behavior in Hanks Solution," Surf. Coat. Tech., vol. 204, 2010, pp. 3636-3640.
Zhang, H., et al., "Laser Shock Processing of 2024-T62 Aluminum Alloy," Mater. Sci. Eng., vol. A257, 1998, pp. 322-327.
Zhang, W., et al., "Micro Scale Laser Shock Peening of Thin Films—Part 1: Experiment, Modeling, and Simulation," ASME, vol. 26, 2004, pp. 10-17.
Zhang, W., et al, "Micro Scale Laser Shock Processing of Metallic Components," ASME, vol. 124, 2002, pp. 369-378.
Zhou, J., et al., "Determination of Thermal Conductivity of Magnesium Alloys," J. Cent. South Univ. Technol., 2001, pp. 60-63.
International Search Report and Written Opinion, dated Nov. 18, 2013, received in connection with International Application No. PCT/US2013/054908.

\* cited by examiner

BIODEGRADABLE MEDICAL DEVICE HAVING AN ADJUSTABLE DEGRADATION RATE AND METHODS OF MAKING THE SAME

CROSS-REFERENCE TO RELATED APPLICATIONS

This application is a divisional of U.S. application Ser. No. 13/966,671, filed Aug. 14, 2013, which is a nonprovisional application claiming priority to U.S. Provisional Patent Application No. 61/682,890, filed Aug. 14, 2012, which are both incorporated herein in their entireties.

STATEMENT REGARDING FEDERALLY SPONSORED RESEARCH OR DEVELOPMENT

This invention was made with government support under grant no. CMMI1000706 awarded by the National Science Foundation. The government has certain rights in the invention.

FIELD OF THE DISCLOSURE

The present disclosure relates generally to a biodegradable medical device made from a biodegradable material having an adjustable rate of degradation. In particular, the present disclosure relates to biodegradable medical devices comprising biodegradable materials (e.g., magnesium-calcium alloys) having an adjustable rate of degradation that can be used in various applications including, but not limited to, drug delivery applications, cardiovascular applications, and orthopedic applications to make biodegradable and biocompatible devices. The present disclosure also relates to methods of making biodegradable medical devices comprising biodegradable materials by using, for instance, hybrid dry cutting/hydrostatic burnishing.

BACKGROUND

Annually several million people suffer bone fractures caused by accidents or disease in the United States alone, resulting in hospitalizations and a notable economic burden on the U.S. health care system. Moreover, the number of bone fractures caused by an age-related disease, such as osteoporosis, may escalate in industrial nations in the coming years with increasing life expectancy. Many of those fractures are too complex for an external medical treatment and must be surgically fixed using internal orthopedic medical devices such as, for example, implants.

Most orthopedic implants in use are composed of metals. Current metallic implants are made of, for instance, titanium, stainless steel, and cobalt-chromium alloys that will not degrade in the human body after implantation because of their high degradation resistance. Those non-degradable metallic implants have certain drawbacks, including, but not limited to, stress shielding and an increased need for secondary surgeries.

Stress shielding arises after implanting, for instance, plates and screws at the site of a bone fracture. Implants and bone form a composite structure where the stress becomes disproportionally carried. Stiffer components carry larger portions of the load. The materials used in current metallic implants are much stiffer (modulus of elasticity ranging from 100-200 gigapascals) than bone tissues (modulus of elasticity ranging from 10-30 gigapascals). As a result, permanent metallic implants shield the bone from carrying stress. Since bone is an efficient living tissue, it adapts itself to new loading conditions by remodeling and becoming less dense in stress shielded areas. This bone remodeling causes pain in patients with non-degradable metallic implants, especially during the first few years after implantation. Furthermore, the resultant decrease in bone density—called artificial osteoporosis by some orthopedic surgeons—is another side effect of stress shielding that weakens the bone and can lead to refractures. Other negative side effects of stress shielding include, but are not limited to, implant loosening, damage to the healing process and adjacent anatomical structures, osteolysis, and chronic inflammation. To decrease negative effects of stress shielding, many patients with non-degradable metallic implants undergo secondary surgeries to repair, revise, or remove their implants.

Examples of other medical devices that can be used, for instance, to fixate a bone fracture, include, but are not limited to, biodegradable polymer devices, autograft devices, isograft devices, xenograft devices, allograft devices, and ceramic devices. Biodegradable polymer devices have certain drawbacks, including, but not limited to, their relatively low mechanical strength and high rate of wear. An implant having sufficient mechanical strength can withstand the stress of load-bearing applications. Allograft, autograft, and isograft devices are made of human tissue and are biocompatible and biodegradable. Allograft devices have certain drawbacks including, but not limited to, their limited supply. Although ceramic devices can have a relatively high mechanical strength, they also have certain drawbacks including, but not limited to, their brittle and non-biodegradable nature. Through degradation and wear, cracks can easily initiate and further propagate until sudden, catastrophic failure, which damages surrounding tissue.

When a bone fractures, the fragments lose their alignment in the form of displacement or angulation. For the fractured bone to heal without deformity, the bony fragments must be realigned to their normal anatomical position. Orthopedic surgeons may attempt to recreate the normal anatomy of the fractured bone by reduction; that is, an orthopedic surgeon can use an implant as a device that is placed over or within bones to hold a fracture reduction.

The degradation rate of a biodegradable medical device can impact its performance. If degradation rate of a biodegradable medical device is faster than healing rate of a bone fracture, the biodegradable medical device will degrade away and be absorbed by body before the healing process is over. This can cause misaligned fragments and ultimately undesirable deformed bony structure. On the other hand, if the degradation rate of the biodegradable medical device is slower than the healing rate of a bone fracture, the biodegradable medical device will still be in place long after the healing process is over. This can cause stress shielding and artificial osteoporosis. The healing rate of a bone fracture depends on a variety of factors including, but not limited to, physiological conditions, age, weight, height, gender, ethnicity, and overall health, and can differ from one application to the other.

The degradation rates of biodegradable medical devices can be adjusted to approximate the healing rate of surrounding tissues in various applications. For instance, one method for adjusting the degradation rate of a biodegradable medical device is by surface treatment, which can be mechanical or non-mechanical. One example of a mechanical surface treatment is laser shock peening (LSP). LSP uses pressure waves formed by plasma expansion to cause plastic deformation of the implant. Other mechanical surface treatments include, but are not limited to, cutting, grinding, indenting, shot peening, micro-forming, and low-plasticity burnishing.

Because some biodegradable materials (for instance, an alloy of Mg—Ca0.8) are soft and can easily be indented or scratched, several mechanical surface treatments may not be capable of processing a surface without causing permanent damage. For example, shots used in a shot peening technique could easily penetrate into the surface of those biodegradable materials, remain on the surface after the process, and cause contamination after implantation. Contamination that would alter the surface biochemistry could result in several short-term and long-term adverse effects. Machining processes may also produce surface contamination that cannot be removed by normal cleaning. Furthermore, shot peening requires a relatively high amount of cold work, and produces relatively low, shallow, and unstable residual stresses.

One example of a non-mechanical method of adjusting the degradation rate of a medical device includes coating the biodegradable medical device to reduce the degradation rate. Coatings may be formed by several processes including, but not limited to, anodizing, chemical vapor deposition, ion implantation, physical vapor deposition, conversion coatings, plating, immersion, and thermal processes. Ensuring the biocompatibility of a coating material is one drawback. Additionally, coatings may not improve the mechanical strength and fatigue life through improved surface integrity.

Other methods to adjust the surface integrity include bulk modification of the biodegradable medical device including, but not limited to, alloying, forming, hot forming, squeeze casting, deep rolling, equal channel angular pressing, and heat treatments. In forming processes—including, but not limited to, rolling, pressing, extruding, and drawing—the ability the impart a favorable surface integrity can be limited by an implant's geometry. Complex implant geometries can be required to treat some bone fracture and may not always be capable of being processed by traditional forming and casting operations.

Accordingly, there is a need for biodegradable medical devices having appropriate stiffness and mechanical strength to overcome challenges associated with other medical devices, for instance, secondary surgical intervention and stress shielding. There is also a need for biodegradable medical devices having an adjustable rate of degradation, and methods of making the same. The compositions and methods disclosed herein address those and other needs.

SUMMARY

Disclosed herein are biodegradable medical devices that comprise biodegradable materials (e.g., magnesium-calcium alloys) having at least one adjustable property chosen from degradation rate, residual stress, hardness, grain size, surface roughness, density, compressive strength, tensile strength, elastic limit, and elongation-at-rupture. Further, disclosed herein is a method for producing a biodegradable medical device by using a surface treatment (e.g., hybrid dry cutting/hydrostatic burnishing or laser shock peening) that involves varying processing parameters including, but not limited to, contact pressure, feed, speed, and strain rate.

Additional advantages of the disclosure will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Biodegradable Implant Material

Figure 1:
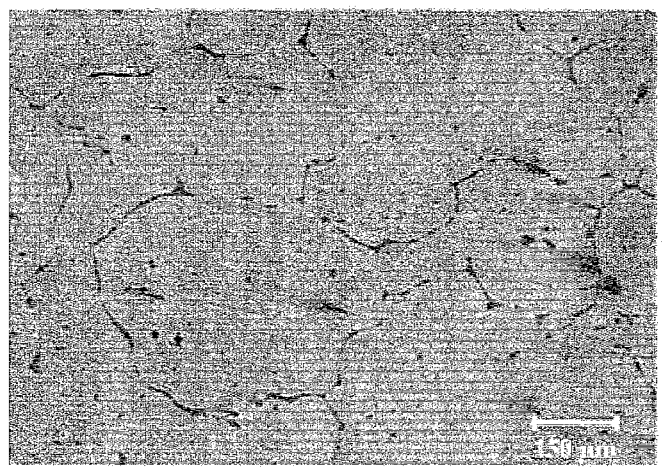
FIG. 1 depicts one embodiment of a microstructure of a biodegradable Mg—Ca0.8 alloy.

Medical devices disclosed herein can comprise a biodegradable material (such as an alloy) that comprises a biodegradable implant material and an alloying element. In one embodiment, the biodegradable implant material is chosen from any material capable of use in a medical device. In another embodiment, the biodegradable implant material is biocompatible. In another embodiment, the biodegradable implant material is non-toxic. In yet another embodiment, the biodegradable implant material is non-carcinogenic. In still another embodiment, the biodegradable implant material is non-mutagenic. In still yet another embodiment, the biodegradable implant material has a modulus of elasticity similar to the modulus of elasticity of bone. In a further embodiment, the biodegradable implant material is lightweight and has a density from 1.6 g/cm$^3$ to 1.8 g/cm$^3$. In another embodiment, the biodegradable implant material is strong such that it has a tensile strength from 100 MPa to 500 MPa.

In one embodiment, the biodegradable implant material includes a metal. In yet another embodiment, the biodegradable implant material includes magnesium. Magnesium (Mg) is an essential element to metabolic activities of the human body and, for instance, an adult human may require an intake of 300-400 mg of magnesium daily. The close modulus of elasticity between magnesium (40 GPa) and bone (10-30 GPa) can minimize stress shielding. Magnesium can degrade significantly in saline media such as human body environment. Without being bound to theory, dissolution of magnesium in chloride-containing media (including, but not limited to, the human body) can happen through the following reaction:

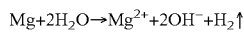

Magnesium can react with water, which is plentiful in bodily fluids, and produce $Mg^{2+}$ ions, hydroxide, and hydrogen gas. In high pH (>11.5) environments, magnesium hydroxide can form a stable protective layer on the surface of medical devices comprising magnesium. In lower pH (<11.5) environments, magnesium hydroxide is unstable and can facilitate degradation of the biodegradable material (such as a magnesium-calcium alloy) in aqueous solution. In some embodiments, the biodegradable implant material including magnesium is present at the implant-bone interface. In some embodiments, the local pH at implant-bone interface is 7.4. In some embodiments, the local pH at the implant-bone interface is less than 7.4, due to, for instance, secondary acidosis resulting from metabolic and resorptive processes after surgery. Without being bound to theory, it is thought that the magnesium hydroxide layer cannot cover an implant's surface in lower pH environments. Therefore, the constant exposure to high chloride-containing electrolyte of the physiological system can cause an accelerated degradation on a biodegradable medical device comprising magnesium in vivo.

Alloying Element

The biodegradable implant material can be alloyed with an alloying element to adjust the degradation rate of the biodegradable implant material. In one embodiment, the alloying element is any element capable of alloying with the biodegradable implant material to adjust the degradation rate of the biodegradable implant material. In another embodiment, the alloying element is biocompatible. In another embodiment, the alloying element is non-toxic and has non-toxic degradation by-products when alloyed with the biodegradable implant material. In yet another embodiment, the alloying element is non-carcinogenic and has non-carcinogenic degradation by-products when alloyed with the biodegradable implant material. In still another embodiment, the alloying element is non-mutagenic and has non-mutagenic degradation by-products when alloyed with the biodegradable implant material. In still yet another embodiment, the alloying element has a density such that the resultant biodegradable material has a similar density to bone.

In one embodiment, the alloying element includes calcium. Calcium (Ca) is a component in human bone that can be essential in chemical signaling with cells. In one embodiment, the calcium is present in an amount sufficient to reduce the rate of degradation of the biodegradable implant material. In another embodiment, the calcium is present in a low enough amount to prevent significant precipitation of an intermetallic phase such as $Mg_2Ca$ on and within grain boundaries. In another embodiment, the calcium is present at an amount equivalent to its maximum solubility in the biodegradable implant material at room temperature. In one embodiment, the calcium is present in the biodegradable material (e.g., magnesium-calcium alloy) in an amount from 0.5 wt % to 3 wt %. In another embodiment, the calcium is present in the biodegradable material in an amount from 0.6 wt % to 1.2 wt %. In yet another embodiment, the calcium is present in the biodegradable material in an amount of 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %, 2.1 wt %, 2.2 wt %, 2.3 wt %, 2.4 wt %, 2.5 wt %, 2.6 wt %, 2.7 wt %, 2.8 wt %, 2.9 wt %, or 3.0 wt %, where any of the stated values can form an upper or lower endpoint of a range. In a specific example, the calcium is present in the biodegradable material (e.g., magnesium-calcium alloy) in an amount of 0.8 wt %. Other alloying elements include, but are not limited to, zinc, aluminum, manganese, silver, gold, nickel, copper, silicon, lithium, indium, gadolinium, cerium, neodymium, lanthanum, yttrium, ytterbium, erbium, dysprosium, praseodymium, and iron.

Biodegradable Medical Device

The biodegradable implant material and alloying element can be alloyed in a biodegradable material, and the biodegradable material can be incorporated into a biodegradable medical device. In one embodiment, calcium is alloyed with magnesium to form a biodegradable material comprising a magnesium-calcium alloy for use in a biodegradable medical device. In another embodiment, 0.8 wt % of calcium is alloyed with magnesium to form a biodegradable material comprising a magnesium-calcium alloy (MgCa0.8) for use in a biodegradable medical device. A biodegradable material comprising a magnesium-calcium alloy can produce dissolved $Mg^{2+}$ ions that can be absorbed or consumed by the human body. Additionally, a biodegradable material comprising a magnesium-calcium alloy can produce dissolved $Ca^{2+}$ ions. Magnesium facilitates the incorporation of calcium into bone. Therefore, the simultaneous release of $Mg^{2+}$ and $Ca^{2+}$ ions from biodegradable materials comprising magnesium-calcium alloys can benefit the bone healing process. Calcium can produce hydroxy-apatite (HA) mineral as a degradation product. Hydroxy-apatite with the formula $Ca_{10}(PO_4)_6(OH)_2$ is a naturally occurring form of calcium apatite and resembles the chemical and mineral components of bone. In one embodiment, hydroxy-apatite stimulates bone cells to attach to the biodegradable medical device surface and promote bone cell adhesion.

Additional components can also be incorporated into the biodegradable material including, but not limited to, zinc, aluminum, manganese, silver, gold, nickel, copper, silicon, lithium, indium, gadolinium, cerium, neodymium, lanthanum, yttrium, ytterbium, erbium, dysprosium, praseodymium, and iron.

The biodegradable material comprising the biodegradable implant material and the alloying element can be incorporated into a variety of medical devices. In one embodiment, the biodegradable medical device is an orthopedic implant. In another embodiment, the biodegradable medical device is a prosthesis. In yet another embodiment, the biodegradable medical device is for use in a cardiovascular application. In still another embodiment, the biodegradable medical device is a drug-delivery device. In a further embodiment, the biodegradable medical device is a diagnostic device. Exemplary biodegradable medical devices include, but are not limited to, orthopedic pins, orthopedic screws, orthopedic plates, replacement joints, bone prostheses, cements, intraosseous devices, pacemakers, drug-supply devices, neuromuscular sensors and stimulators, replacement tendons, subperiosteal implants, ligation clips, electrodes, artificial arteriovenous fistulae, heart valves, vascular grafts, internal drug-delivery catheters, ventricular-assist devices, laparoscopes, arthroscopes, draining systems, dental cements, dental filling materials, skin staples, intravascular catheters, ulcer tissue dressing, burn tissue dressing, granulation tissue dressing, intraintestinal devices, endotracheal tubes, bronchoscopes, dental prostheses, orthodontic devices, intrauterine devices, and healing devices.

The biodegradable medical device can be configured for use in different patients. In one embodiment, the biodegradable medical device is configured for use in applications for adult humans. In another embodiment, the biodegradable medical device is configured for use in pediatric applications. In yet another embodiment, the biodegradable medical device is configured for use in veterinary applications. In some embodiments, the biodegradable medical device is configured to match the healing rate of a patient. The healing rate of a bone fracture depends on a variety of factors including, but not limited to, physiological conditions, age, weight, height, gender, ethnicity, and overall health. Thus, the healing rate and configuration of the biodegradable medical device can differ from one application to the other.

Surface Treatment

The biodegradable medical device can be surface treated to further adjust the properties and the biological response of the biodegradable medical device. The biodegradable medical device properties that can be modified by surface treatment include, but are not limited to, residual stress, hardness, grain size, surface roughness, compressive strength, tensile strength, elastic limit, elongation-at-rupture, and degradation rate as well as their profiles below the surface. Profiles below the surface include, but are not limited to, the depth that the previously mentioned properties extend at well as the depth of their maximums and minimums.

The biodegradable medical device properties can be adjusted by tuning the processing conditions used in the surface treatment including, but not limited to, contact pressure, feed, speed, strain rate, laser power, ball size, number of passes, pattern, temperature, dent spacing, and focal length. The surface treatment can be any surface treatment that can adjust the surface and near surface properties of the biodegradable medical device. Exemplary surface treatments include, but are not limited to, laser shock peening, shot peening, dry cutting, hydrostatic burnishing, or combinations thereof.

Figure 2:
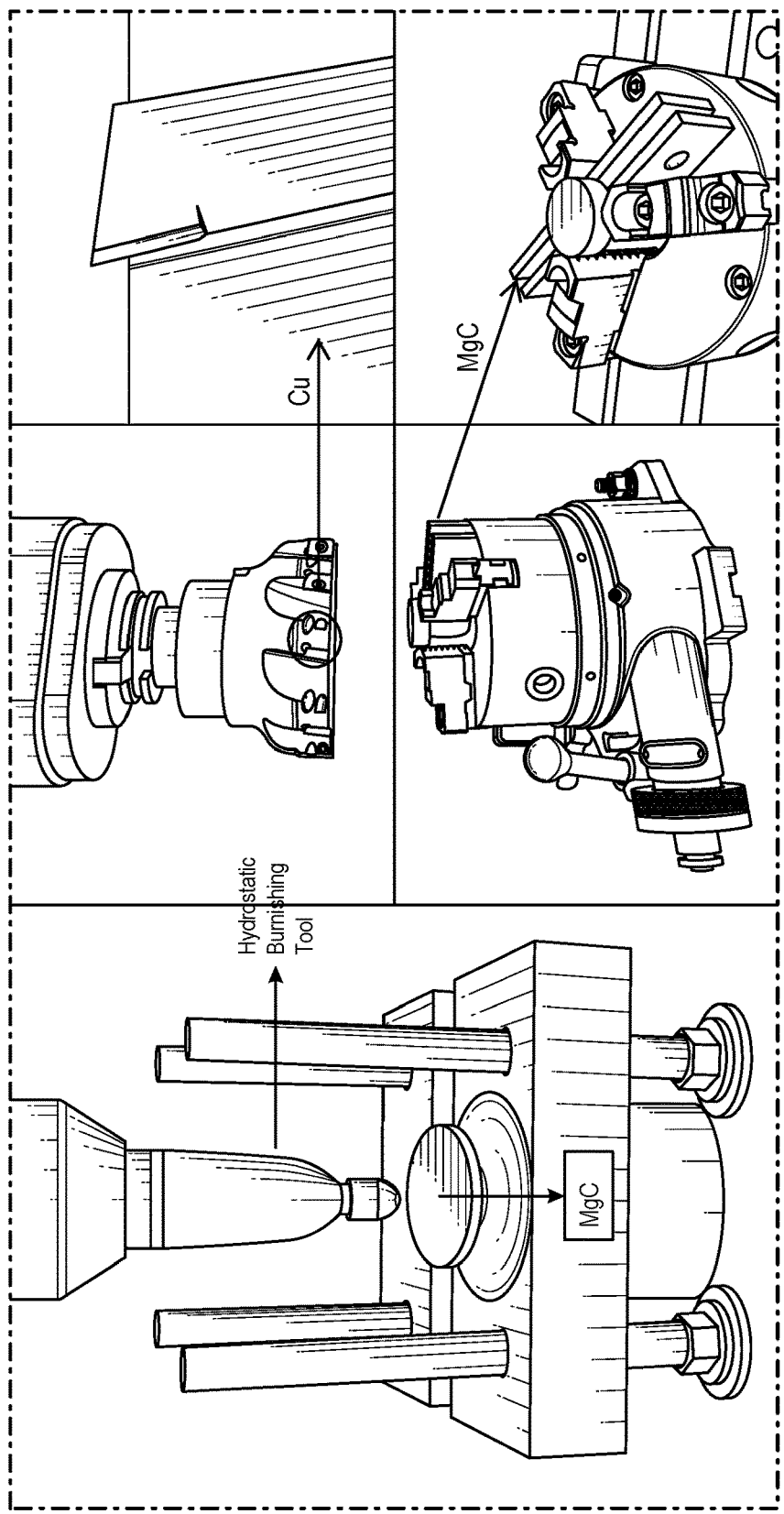
FIG. 2 depicts one embodiment of a setup that can be used to surface treat a medical device by hybrid dry cutting/hydrostatic burnishing.
Figure 8:
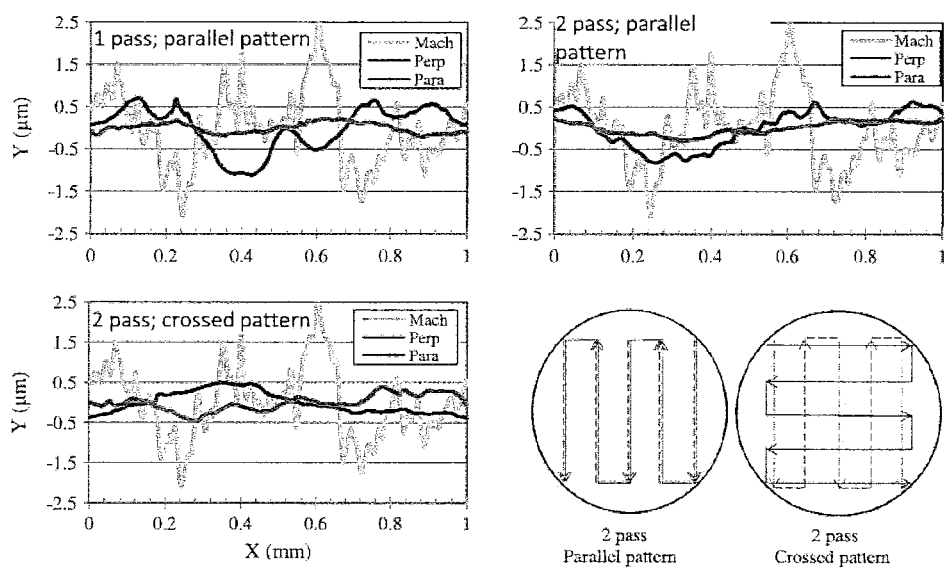
FIG. 8 depicts embodiments of surface profiles.

In one embodiment, the biodegradable medical device is surface treated by hybrid dry cutting/hydrostatic burnishing to adjust the degradation rate of the biodegradable medical device. In some embodiments, hybrid dry cutting/hydrostatic burnishing is tuned during the biodegradable medical device manufacturing stage to adjust surface integrity in such a way that the resultant degradation rate approximates the healing rate for a certain orthopedic application. FIG. 2 depicts one embodiment of a setup that can be used to surface treat a biodegradable medical device by hybrid dry cutting/hydrostatic burnishing. FIG. 8 depicts embodiments of various surface profiles that can be achieved using the surface treatments disclosed herein. In the hybrid dry cutting/hydrostatic burnishing technique, material cutting and forming can be performed on the same computer numerical controlled (CNC) machine sequentially or simultaneously; thus, the initial investment on hardware can be lower than other techniques.

Material cutting includes removing material on the surface of a biodegradable medical device by sharp cutting tools in incremental layers either with or without cutting fluids. In FIG. 2—which depicts one embodiment of a setup that can be used to surface treat a medical device by hybrid dry cutting/hydrostatic burnishing—the cutting tool is equipped with nine diamond cutting inserts that spin at very high speeds. The biodegradable medical device is firmly fixed using the three-jaw chuck. As the tool is lowered, it engages the workpiece and begins removing a layer of material. The depth of this engagement is known as the depth-of-cut. During the cutting process, part of the surface on a biodegradable medical device is removed via chip formation while the freshly formed surface is simultaneously plowed over by the cutting tool. With properly chosen cutting conditions, the newly plowed surface can have a surface integrity that changes the mechanical properties and biological response of a biodegradable medical device. Tunable cutting parameters depend on the alloy being machined and include, but are not limited to, spinning speed of the tool, horizontal speed of the tool (feed), depth-of-cut, cutting tool material and its geometry.

Cutting processes can generate considerable amounts of heat. Thus, cutting fluids can be used. Still, their widespread use is controversial because of the ecological issues that arise. In the case where no cutting fluids are used, the process is known as dry cutting. Using diamond cutting inserts on, for instance, magnesium alloys (which are comparatively soft), can make eco-friendly, dry cutting feasible.

After dry cutting, material forming via burnishing can shape the biodegradable medical device into final form without removing material. In the embodiment shown in FIG. 2, the tooling can be changed in the CNC machine so that hydrostatic burnishing tool can be installed. The surface of the biodegradable medical device can then be burnished using predetermined burnishing process parameters to provide the desired surface integrity. Hydrostatic burnishing includes a smooth free-rolling ceramic ball that is pressed against and rolled along the surface of the work piece using a pressurized hydraulic cushion. As the result, it deforms the work piece surface into a state of compression. This process is characterized by the combination of, for instance, the following three physical effects: (i) deep and stable compressive residual stresses, (ii) work hardening and increase in microhardness, and (iii) burnishing or decreasing surface roughness. The tunable process parameters in burnishing that can adjust properties of the biodegradable medical device include, but are not limited to, contact pressure, feed, speed of movement in horizontal plane, overlap/feed, tool geometry (ceramic ball diameter), burnishing pattern, and temperature.

In one embodiment, the desired surface integrity from a practitioner is to have a smooth surface finish and a degradation rate of 1 mm/yr. To achieve those properties, a maximum residual stress of −150 MPa approximately 0.5 mm from the surface as well as a microhardness of at least 50 HV is required. Thus according to FIG. 3, a biodegradable medical device that is surface treated by burnishing at a contact pressure of 2.1 GPa, feed of 0.1 mm, and a strain rate of $10^1$ s$^{-1}$ will provide the desired surface integrity and corrosion rate.

In one embodiment, the surface treatment includes any treatment that can adjust the degradation rate of a biodegradable medical device. In another embodiment, the surface treatment includes any treatment that can adjust the degradation rate of the biodegradable medical device to match that of the healing rate of a bone fracture such that a patient heals at the same rate that the patient's biodegradable medical device degrades. In some embodiments, the surface treatment induces compressive residual stress into at least a portion of the biodegradable medical device (e.g., on or below the surface of the biodegradable medical device or a portion thereof). In some embodiments, the surface treatment induces porous surface microstructure in at least a portion of the biodegradable medical device.

In another embodiment, the surface treatment alters the topography of at least a portion of the biodegradable medical device. In another embodiment, the surface treatment produces refined grains in at least a portion of the biodegradable medical device. In another embodiment, the surface treatment produces a better surface finish in at least a portion of the biodegradable medical device. In yet another embodiment, the surface treatment creates a geometric benefit in at least a portion of the biodegradable medical device that assists in the healing process. In one embodiment, the surface treatment provides a porous structure in at least a portion of the biodegradable medical device that is favorable for cell adhesion and growth between the biodegradable medical device and bone. Exemplary input variables that can adjust the biodegradable medical device properties include, but are not limited to, contact pressure, feed, speed, and strain rate, discussed in more detail below.

Contact Pressure

Figure 3:
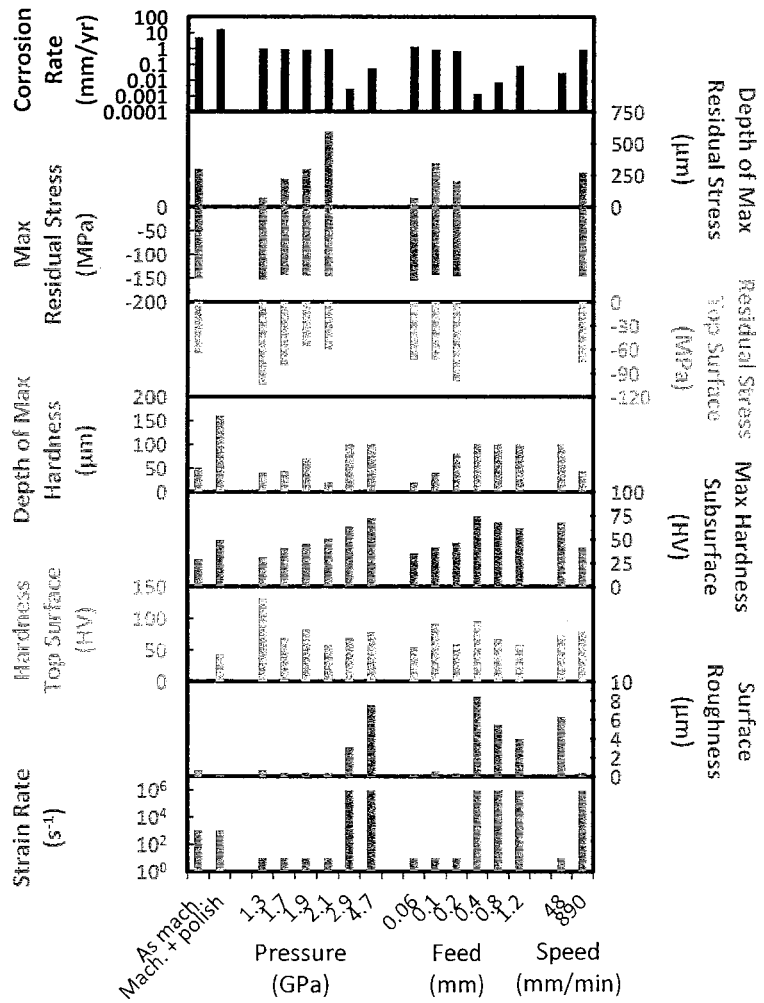
FIG. 3 depicts exemplary adjustments to processing parameters (e.g., contact pressure, feed, speed, strain rate) and the resulting changes in medical device properties (e.g., degradation rate, max residual stress, depth of max hardness, hardness on top surface, surface roughness, max hardness of subsurface, residual stress on top surface, and depth of max residual stress).

The contact pressure used in the surface treatment can be adjusted. For instance, the contact pressure can be adjusted to from 1 gigapascal to 5 gigapascals (e.g., from 1.3 gigapascals to 2.1 gigapascals, from 2.1 gigapascals to 4.7 gigapascals, from 2.9 gigapascals to 4.7 gigapascals). FIG. 3 depicts examples of how adjusting the contact pressure can change the biodegradable medical device properties (e.g., degradation rate, maximum residual stress, depth of maximum hardness, hardness on top surface, surface roughness, maximum hardness of subsurface, residual stress on top surface, and depth of maximum residual stress). The contact pressure can be adjusted by increasing or decreasing desired force or power. Adjustments to the contact pressure can be changed using a computer program that controls the desired surface treatment process. The contact pressure can be adjusted such that a desired surface integrity is achieved to accommodate a patient's conditions. In one embodiment, a practitioner would conduct a bone density (BMD) scan to indicate if a patient has osteoporosis or is a fracture risk. Depending on the severity indicated on that bone density scan, a practitioner would request a biodegradable medical device suitable for the patient's needs. Biodegradable medical devices processed with a high contact pressure are desirable for patients with low bone density because they may not produce fast, new bone growth and thus may require a slow biodegradable medical device.

According to the National Osteoporosis Foundation, the higher risk groups for low bone density include the elderly, menopausal and post-menopausal women, patients with a family history of low bone density, patients with a low body weight or eating disorders, and patients who have had a fracture as an adult. In another embodiment, the practitioner would decide based on patient factors including, but not limited to, age, weight, medical history, gender, medical condition, and health, that the patient needs a biodegradable medical device that degrades at a rate based on a preset scale from 1 to 5, where 1 indicates a slow corrosion rate, 3 indicates a moderate corrosion rate, and 5 indicates a rapid corrosion rate. In another embodiment, a practitioner who is treating a child for a fracture would request a biodegradable medical device that had a faster corrosion rate. A faster corrosion rate is accomplished by using lower contact pressures. In yet another embodiment, the location and orientation of the fracture and subsequent fracture treatment may require one or more surfaces of the biodegradable medical device to be processed at one or more contact pressures such the biodegradable medical device has unique properties at one or more locations on the surface.

One or more unique properties include, but are not limited to, residual stress, microhardness, corrosion rate, fatigue life, and fracture toughness. An example of the previously mentioned embodiment is a patient who is obese and suffered a bone fracture. The obese patient may distribute stresses differently in their bones and consequently affect the healing process. A biodegradable medical device in the form of a plate aligned along the femur of an obese patient may cause a higher bending or torsional stress as opposed to pure axial stress. In such a case, a practitioner may require a biodegradable medical device that is stronger and/or weaker on at least one or more portions of one or more surfaces to control the device's degradation in a way that accounted for the stress distribution of the obese patient. This can be accomplished by changing the contact pressure used during the surface treatment on at least one or more portions of one or more surfaces of the biodegradable medical device that best suited the patient's needs.

If an obese patient carried more stress along the medial side of the femur, a biodegradable medical device on the medial side of the femur can be processed at a higher contact pressure so that the later residual stress and microhardness increase the fracture toughness and fatigue life of the device. In yet another embodiment, the location and orientation of the fracture and later fracture treatment may require one or more surfaces of the biodegradable medical device to be processed at one or more contact pressures such the biodegradable medical device corrodes at one or more locations in one or more desired directions. Degrading at different corrosion rates in one or more directions is accomplished by establishing a gradient of the previously mentioned surface integrity properties. A gradient can be achieved in a specific location by varying the contact pressure while moving either the biodegradable medical device or tooling.

Feed

The feed is the distance of relative lateral movement between the tool and a biodegradable medical device. In the case of burnishing, the feed is the center-to-center distance between successive burnishing tracks. In laser shock peening, the feed is the center-to-center spacing between successive peens. The feed used in the surface treatment can be adjusted. For instance, the feed can be adjusted to from 0.06 millimeters to 1.2 millimeters (e.g., from 0.06 millimeters to 0.4 millimeters, from 0.4 millimeters to 1.2 millimeters). FIG. 3 depicts examples of how adjusting the feed can change the biodegradable medical device properties (e.g., degradation rate, max residual stress, depth of max hardness, hardness on top surface, surface roughness, max hardness of subsurface, residual stress on top surface, and depth of max residual stress).

The feed can be adjusted by changing a computer program that controls the movements of the tool. The suitable feed for a patient depends on factors including, but not limited to, the desired surface roughness and corrosion rate. For a young patient, a feed of 1.2 mm using a high strain-rate process or 0.06 mm to 0.2 mm using a low strain-rate process can be desirable because young patients produce new bone faster than adults and would thus need a fast-degrading implant. However, elderly patients and those who show signs of low bone density may require a biodegradable medical device that had been processed at a feed of 0.4 mm and a high strain-rate so that the implant would degrade as slowly as possible. Depending on the type and location of fracture as well as the general health of the patient, the practitioner may desire an implant with a rough surface. Adjusting the feed produces surfaces with a different roughness that can promote bone-implant adhesion and ingrowth. Also, the location and orientation of the fracture and later fracture treatment may require the surface of the implant to be processed at a specific feed such the biodegradable medical device corrodes at a specific location or in a desired direction.

Speed

The speed refers to the velocity of the tool used in processing the biodegradable medical device. For example, the speed of the burnishing tool. The speed used in the surface treatment can be adjusted. For instance, the speed can be adjusted from 50 millimeters per minute to 900 millimeters per minute (e.g., from 100 millimeters per minute to 800 millimeters per minute, from 300 millimeters per minute to 600 millimeters per minute). FIG. 3 depicts examples of how adjusting the speed can change the biodegradable medical device properties (e.g., degradation rate, max residual stress, depth of max hardness, hardness on top surface, surface roughness, max hardness of subsurface, residual stress on top surface, and depth of max residual stress).

The speed can be adjusted by changing a computer program that controls the movements of the tool. The speed can adjust the corrosion rate of the biodegradable medical device. In one embodiment, a practitioner may require a device processed at high speeds for young and/or patients with adequate bone density. At high speeds, the corrosion rate is faster, which is ideal for patients who generate new bone more rapidly. At low speeds, the corrosion rate is slower, which is ideal for patients who do not generate new bone rapidly. The desired healing profile is what a practitioner would provide a manufacturing engineer. The engineer knowing the correlations between various process parameters, surface integrity characteristics, and degradation rates decides which parameter to adjust and how much so that after implantation, the healing rate and degradation rate match. Also, the location and orientation of the fracture and later fracture treatment may require the surface of the implant to be processed at one or more speeds such the biodegradable medical device corrodes differently at one or more locations or in one or more desired directions.

Strain Rate

The strain rate describes the rate of material deformation and is often determined by the manufacturing process. The strain rate when processing a biodegradable medical device and consequent surface integrity properties can be adjusted by using one or more manufacturing processes. For example, the strain rates for burnishing and laser shock peening processes are on the order of $10^1$ s$^{-1}$ and $10^6$ s$^{-1}$, respectively. Therefore, the strain rate can be adjusted to from 10 s$^{-1}$ to $10^6$ s$^{-1}$ (e.g., from $10^2$ s$^{-1}$ to $10^5$ s$^{-1}$, from $10^3$ s$^{-1}$ to $10^4$ s$^{-1}$). FIG. 3 depicts examples of how adjusting the strain rate can change the biodegradable medical device properties (e.g., degradation rate, max residual stress, depth of max hardness, hardness on top surface, surface roughness, max hardness of subsurface, residual stress on top surface, and depth of max residual stress). Based on a patient's age, weight, and gender, a practitioner would select a device processed at a specific strain rate that caused said device to initiate and propagate degradation at a predetermined rate that suitably matches the needs of the patient. Patients with known bone diseases or low bone density, such as elderly women, would require an implant processed at a high strain rate, which would cause a slow corrosion rate. Patients with healthy bone would need an implant processed at a low strain rate, which would cause a faster corrosion rate. Patients who are overweight or suffer from a bone disease may distribute stress differently with their body. Therefore, said patients may require an implant processed at one or more locations on the biodegradable medical device, which can either delay the onset of corrosion or accelerate the onset of corrosion to match their needs in terms of healing and stress distribution.

Adjustable Properties

Each combination of surface treatment variables leaves behind unique properties that define the surface integrity on and near the surface of a biodegradable medical device. The properties of the biodegradable medical device can be adjusted in a variety of ways. In some embodiments, the amount of the alloying element can be adjusted to affect the properties of the biodegradable medical device. In some embodiments, the surface treatment can be adjusted to affect the properties of the biodegradable medical device. Exemplary properties that can be adjusted by the amount of alloying element and/or surface treatment include, but are not limited to, hardness, grain size, surface roughness, density, residual stress, compressive strength, tensile strength, elastic limit/elastic modulus, elongation-at-rupture, fracture toughness, fatigue life, and degradation rate. In some embodiments, the alloying element is calcium and the amount of calcium is adjusted to affect the properties of a magnesium-calcium alloy. In some embodiments, the surface treatment (e.g., hybrid dry cutting/hydrostatic burnishing) is adjusted to affect the properties of a biodegradable medical device comprising a biodegradable material comprising a magnesium-calcium alloy. FIG. 3 depicts examples of how adjusting the processing parameters of the surface treatment (e.g., contact pressure, feed, speed, and strain rate) can change the biodegradable medical device properties (e.g., degradation rate, max residual stress, depth of max hardness, hardness on top surface, surface roughness, max hardness of subsurface, residual stress on top surface, and depth of max residual stress).

Degradation Rate

Degradation rate is a measure of how quickly the biodegradable medical device degrades in the human body. The degradation rate of the biodegradable medical device can be impacted by the degradation resistance of the biodegradable material (e.g., a biodegradable material comprising a magnesium-calcium alloy). For example, the degradation resistance of a biodegradable material comprising a magnesium-calcium alloy decreases with increasing amount of calcium, which is related to Mg$_2$Ca precipitates on grain boundaries and within grains. In one embodiment, a biodegradable material comprising a magnesium-calcium alloy with 0.8 wt % calcium can be used to obtain an optimum combination of mechanical strength, plasticity, ductility, and degradation rate by alloying. In one embodiment, the 0.8 wt % of calcium concentration is the maximum solubility of calcium in a magnesium lattice at room temperature. FIG. 1 shows an embodiment of the microstructure of a Mg—Ca0.8 alloy. When calcium is alloyed in an amount of 0.8 wt %, Mg$_2$Ca can precipitate on grain boundaries and inside the grains can promote more moderate and uniform rather than fast and localized degradation. In another embodiment, the calcium content is less than 0.8 wt %, which can yield less ductility and mechanical strength. In yet another embodiment, the calcium content is greater than 0.8 wt %, which can cause Mg$_2$Ca precipitation and ultimately decreased degradation resistance due to feasibility of galvanic degradation.

Figure 4:
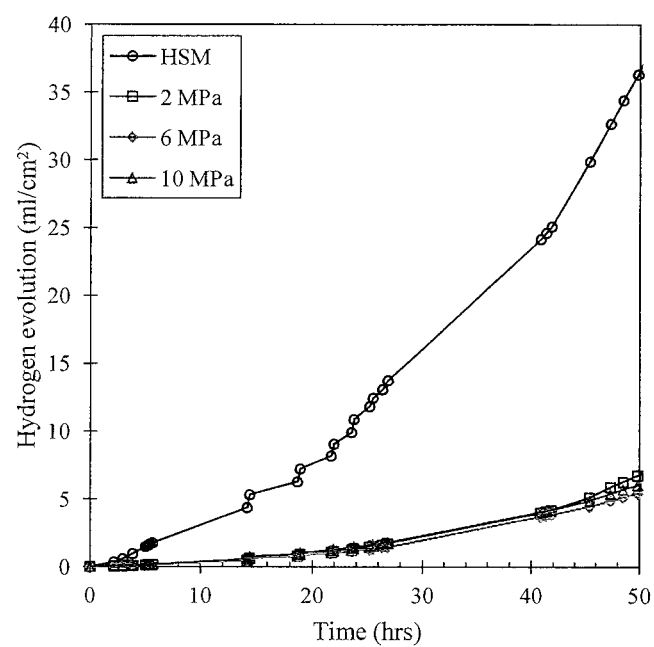
FIG. 4 depicts one embodiment of the degradation of surface treated biodegradable Mg—Ca0.8 implants in simulated body fluid at 50 hours.
Figure 5:
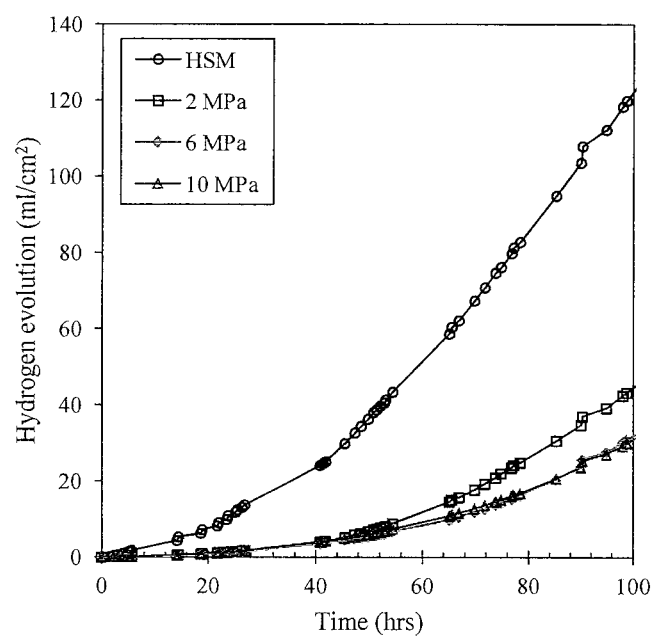
FIG. 5 depicts one embodiment of the degradation of surface treated biodegradable Mg—Ca0.8 implants in simulated body fluid at 100 hours.
Figure 6:
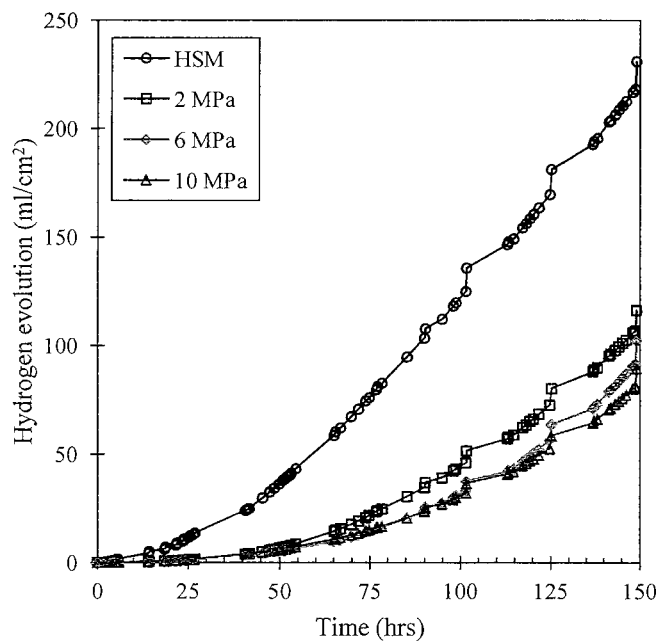
FIG. 6 depicts one embodiment of the degradation of surface treated biodegradable Mg—Ca0.8 implants in simulated body fluid at 150 hours.
Figure 7:
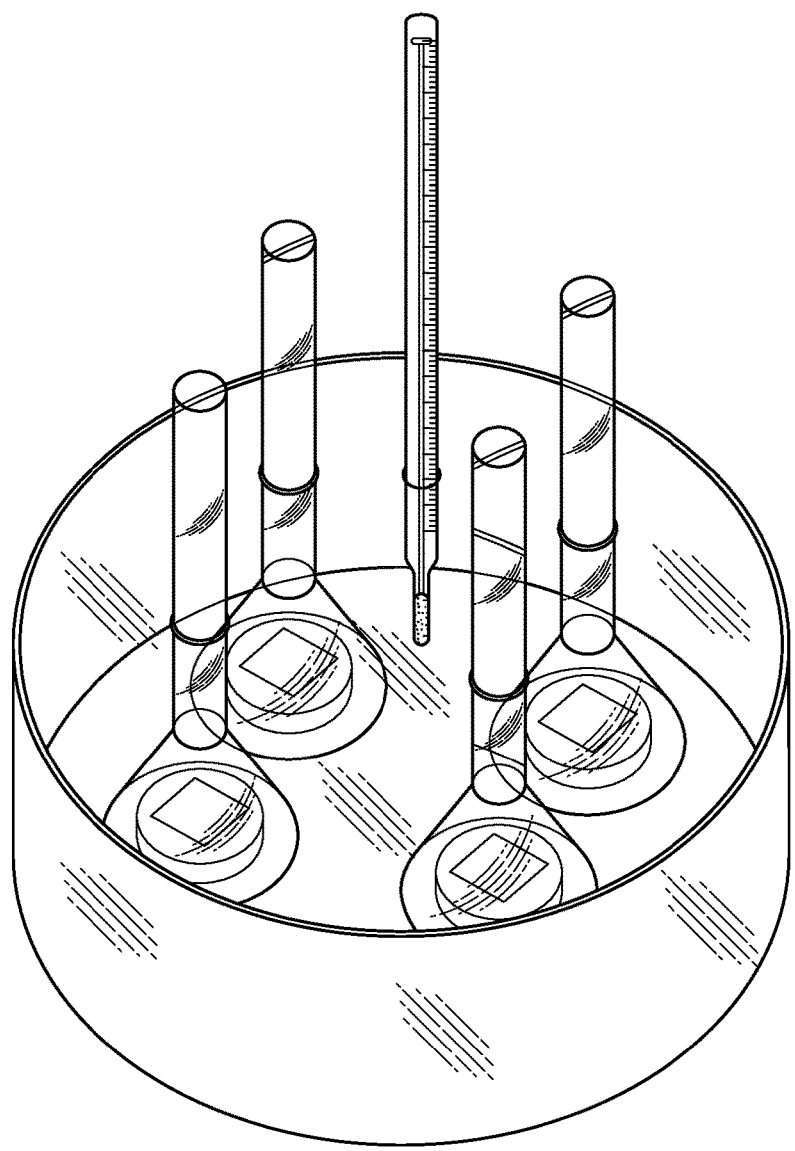
FIG. 7 depicts one embodiment of a setup that can be used for eudiometry.

During magnesium dissolution of a magnesium-containing biodegradable medical device, hydrogen gas is produced at the same rate that magnesium dissolves. As such, eudiometry of hydrogen can be used to determine long term degradation behavior of Mg—Ca0.8 implants in simulated body fluid. FIG. 7 depicts one embodiment of a setup that can be used for eudiometry. FIGS. 4-6 depict exemplary data of the degradation of Mg—Ca0.8 implants processed by dry cutting and hybrid dry cutting/hydrostatic burnishing under different process parameters. The added burnishing treatment after dry cutting can decrease the degradation rate of the biodegradable medical device. Also, increasing the contact pressure can further decrease the corrosion rate. These results shown in FIGS. 3-6 confirm hybrid dry cutting/hydrostatic burnishing is one embodiment of a manufacturing process that can alter the corrosion rate of a biodegradable medical device.

In one embodiment, the degradation rate of the biodegradable medical device is adjusted by alloying. In another embodiment, the degradation rate of the biodegradable medical device is adjusted by surface treatment of the biodegradable medical device. In yet another embodiment, the degradation rate of the biodegradable medical device is adjusted by surface treatment and alloying. In another embodiment, the degradation rate of the biodegradable medical device is adjusted to match that of the healing rate of bone such that a patient heals at the same rate that the patient's biodegradable medical device degrades. The healing rate of bone in a patient can be approximated by any method known in the art. For instance, the healing rate of bone in a patient can be found in textbook references that are known to those of ordinary skill in the art. For example, the degradation rate can be adjusted to from 0.001 millimeter per year to 20 millimeters per year (e.g., from 0.01 millimeters per year to 10 millimeters per year, from 0.1 millimeters per year to 1 millimeters per year).

Two methods to measure degradation rate include: (1) immersion test and (2) potentiodynamic test. In an immersion test, the evolved hydrogen is collected over time and then using the stoichiometry of the degradation reaction, degradation rate is calculated. In potentiodynamic test, corrosion current density is measured using electrochemistry principals and then the current density is converted to degradation rate using Faraday's law.

Density

Density is a measure of a material's mass per unit volume. In one embodiment, the density of the biodegradable material in the biodegradable medical device is from 1.5 g/cm$^3$ to 3.5 g/cm$^3$. In another embodiment, the density of the biodegradable material in the biodegradable medical device is from 1.7 g/cm$^3$ to 2.0 g/cm$^3$. The bulk density of a biodegradable medical device can be altered by changing the compositional elements that make up the alloy.

Residual Stress

Figure 13:
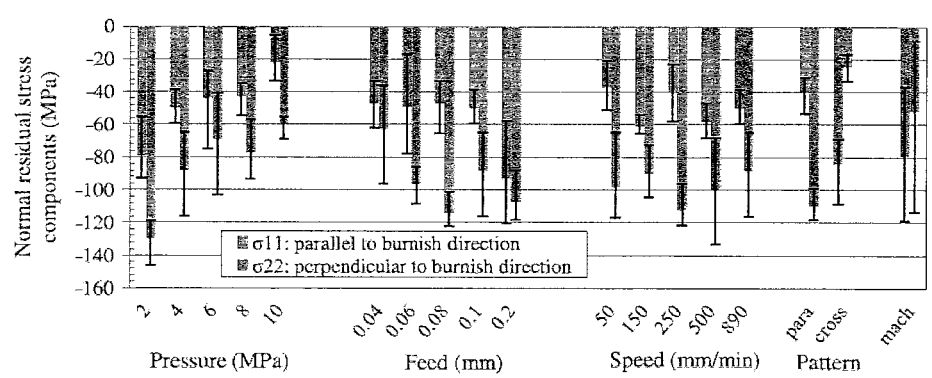
FIG. 13 depicts exemplary effects of burnishing parameters on residual stress.

Residual stresses are those stresses that remain on or near the surface of a biodegradable medical device after a surface treatment. In some embodiments, the surface treatment induces residual stress into at least a portion of the biodegradable medical device (e.g., on or below the surface of the biodegradable medical device or a portion thereof). For example, the residual stress can be from −170 megapascals to −20 megapascals (e.g., from −160 megapascals to −50 megapascals, from −150 megapascals to −100 megapascals). The residual stress can have a maximum depth in the biodegradable medical device. For example, the maximum residual stress depth can be from 5 micrometers to 600 micrometers (e.g., from 10 micrometers to 500 micrometers, from 20 micrometers to 400 micrometers, from 50 micrometers to 300 micrometers, from 150 micrometers to 250 micrometers). One method to measure residual stress is by x-ray diffraction. Changing the process parameters of a surface treatment affects the resulting magnitude and depth of the residual stress on and below the surface. For example, increasing the contact pressure causes the depth of the maximum residual stress to increase. FIGS. 3 and 13 depict exemplary effects of various burnishing parameters on residual stress.

Grain Size

Metals, except in a few instances, are crystalline in nature and, except for single crystals, contain internal boundaries known as grain boundaries. When a new grain is nucleated during processing (as in solidification or annealing after cold working, for example), the atoms within each growing grain are lined up in a specific pattern that depends upon the crystal structure of the metal or alloy. With growth, each grain will eventually impinge on others and form an interface where the atomic orientations are different.

Mechanical properties can be adjusted as the size of the grains is changed. Alloy composition and processing (either bulk or on the surface) can be adjusted to achieve the desired grain size. For example, the grain size can be adjusted to from 100 micrometers to 700 micrometers (e.g., from 200 micrometers to 600 micrometers, from 300 micrometers to 500 micrometers). ASTM E112 standard is used to determine average grain size. In most metals and their alloys, a smaller grain size can increase the strength of a material.

Surface Roughness

Figure 9:
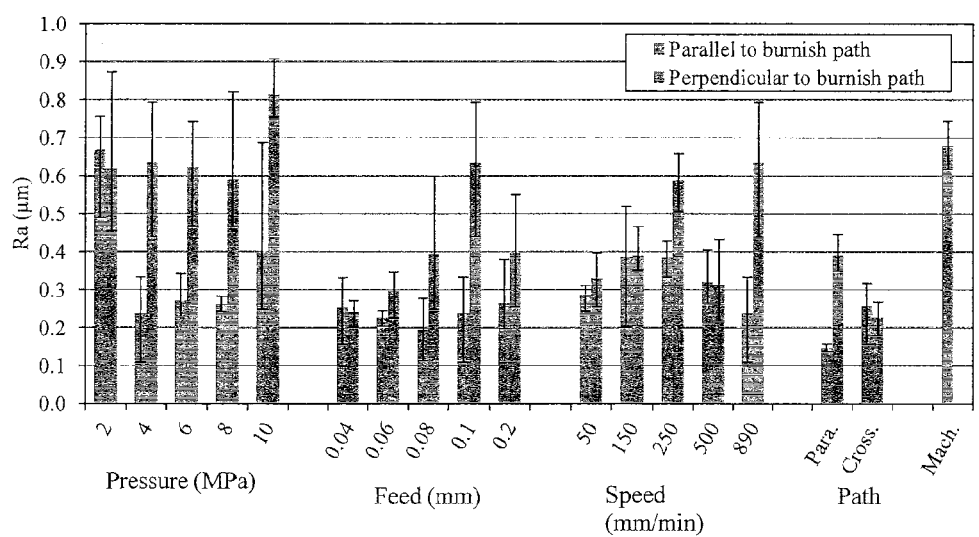
FIG. 9 depicts exemplary effects of burnishing parameters on surface roughness.
Figure 10:
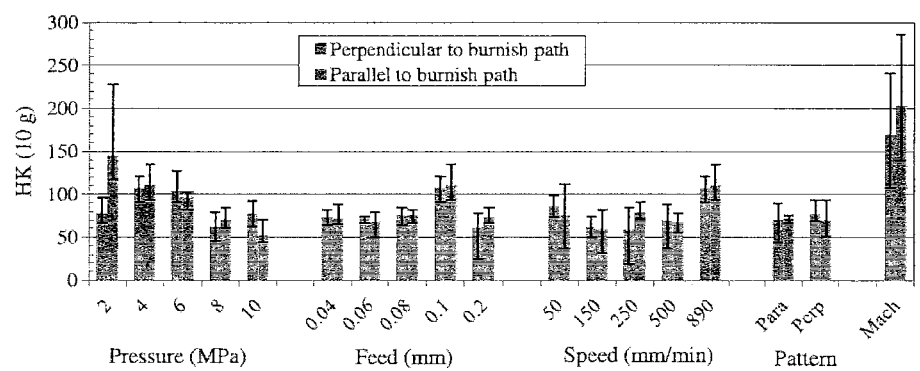
FIG. 10 depicts exemplary effects of burnishing parameters on surface microhardness.
Figure 11:
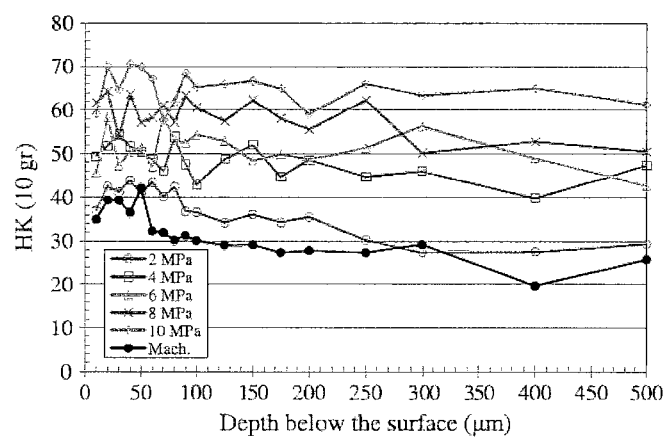
FIG. 11 depicts exemplary effects of hydraulic burnishing pressure on subsurface microhardness.
Figure 12:
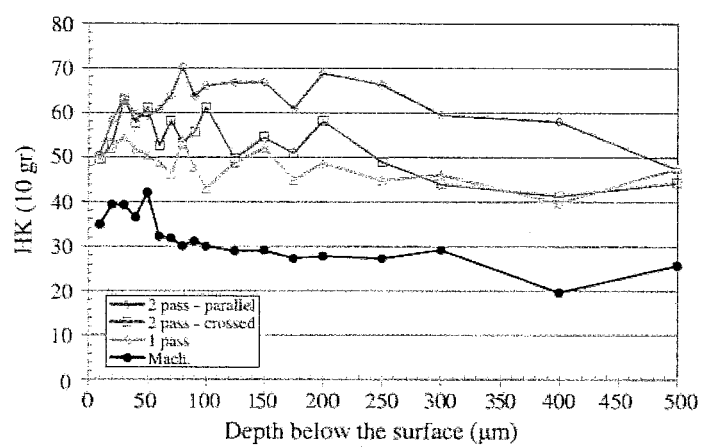
FIG. 12 depicts exemplary effects of burnishing pass and pattern on subsurface microhardness.

Surface roughness is a measure of the texture of the surface. Surface roughness can be adjusted to change the biodegradable medical device properties. For example, the surface roughness can be adjusted to 10 micrometers or less (e.g., 8 micrometers or less, 6 micrometers or less, 4 micrometers or less). The surface roughness can be measured using either a laser or a mechanically contacting profilometer. The surface roughness largely depends on the nature of deformation during a surface treatment. Process parameters such as contact pressure, feed and speed can drastically influence the resulting roughness profile. For example, burnishing typically creates a roughness on the order of 100's of nanometers, while laser shock peening is more on the order of 10's of micrometers. A rough profile may be more desirable for bone-ingrowth applications while a smooth profile may be preferred in arterial flow applications. FIGS. 3 and 9 depict exemplary effects of burnishing parameters on surface roughness.

Tensile/Compressive Strength

Strength is a measure of the maximum stress that a material can withstand while being stretched (tension) or squeezed (compression) without failing. Alloying magnesium with calcium increases the tensile strength of the resultant biodegradable medical device. In one embodiment, magnesium is alloyed with low amounts of calcium to increase the tensile strength of the biodegradable medical device. In another embodiment, magnesium is alloyed with calcium in an amount less than or equal to 4.0 wt % to increase the tensile strength of the biodegradable medical device to an amount of less than or equal to 240 MPa. ASTM E8 standard is used to determine tensile strength of metallic materials.

Elastic Limit or Elastic Modulus

Elastic limit (i.e., elastic modulus) is a measure of plasticity. In one embodiment, the elastic limit of the biodegradable medical device is from 10 gigapascals (GPa) to 80 GPa. In another embodiment, the elastic limit of the biodegradable material (e.g., a biodegradable material comprising a magnesium-calcium alloy) is from 30 GPa to 60 GPa. In a further embodiment, the elastic limit of the biodegradable material (e.g., a biodegradable material comprising a magnesium-calcium alloy) is from 40 GPa to 50 GPa. The content of calcium as an alloying element affects the 0.2% elastic limit, as shown in FIG. 1. In embodiments having low calcium content, the elastic limit is 80 MPa lower than tensile strength. This can indicate relatively high plasticity. With increasing amount of calcium, for instance amounts of at least 2.0 wt %, plasticity decreases and without significantly effecting tensile strength. ASTM E8 standard is used to determine elastic limit of metallic materials.

Elongation-at-Rupture

Elongation-at-rupture is a measure of ductility. The amount of the alloying element, such as calcium, can also affect the elongation-at-rupture and ductility as well. There is a continuous decrease in elongation-at-rupture and ductility above 1.0 wt % Ca. Considerable precipitation of brittle $Mg_2Ca$ intermetallic phase on grain boundaries and inside grains is responsible for this decline in ductility above 1.0 wt % Ca. ASTM E8 standard is used to determine elongation-at-rupture of metallic materials.

Hardness

Hardness can be adjusted in the biodegradable medical device. In some embodiments, the surface treatment adjusts the hardness of at least a portion of the biodegradable medical device (e.g., on or below the surface of the biodegradable medical device or a portion thereof). For example, the hardness can be of from 40 HV to 140 HV (e.g., from 45 HV to 125 HV, from 50 HV to 100 HV, from 55 HV to 75 HV). The hardness can have a maximum depth in the biodegradable medical device. For example, the maximum hardness depth can be from 5 micrometers to 175 micrometers (e.g., from 10 micrometers to 150 micrometers, from 15 micrometers to 125 micrometers, from 25 micrometers to 100 micrometers, from 40 micrometers to 75 micrometers). ASTM E92-82 and E384-06 standards are used to measure hardness. FIGS. 3 and 10-12 depict embodiments of the effects of various burnishing parameters on microhardness.

Other than in the examples, or where otherwise noted, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the examples are reported as precisely as possible. Any numeric value, however, inherently contains certain errors necessarily resulting from the standard deviation found in their respective testing methods. Finally, the various titles and section headers used throughout the specification are presented merely for the convenience of the reader and are not intended to limit the disclosure. The disclosure herein is not limited to specific methods or reagents. Further, the terminology used herein is for the purpose of describing particular aspects only and is not intended to be limiting.

By way of non-limiting illustration, examples of certain embodiments of the present disclosure are given below.

EXAMPLES

Example 1: Adjusting Degradation Rate of Mg—Ca0.8 Samples Using Hybrid Dry Cutting/Hydrostatic Burnishing Treatment FIG. 2 shows an exemplary hybrid dry-cutting/hydrostatic burnishing setup. In hybrid technique material cutting and material forming are combined and are performed on same Cincinnati Arrow 500 CNC milling machine sequentially or simultaneously. Material cutting is removing material from the workpiece by sharp cutting tools until the final shape of the device is attained. Material forming is shaping the workpiece into final form without material removal.

Calcium (Ca) was alloyed with magnesium (Mg) to form a binary Mg—Ca alloy. Mg alloyed with 0.8 weight percent Ca (Mg—Ca0.8) was prepared using pure Mg of ASTM grade 9980A and Mg-30% Ca master alloy. The pure Mg was melted down at 650° C. Next, the melt was heated to 710° C. and Mg-30% Ca was added until the target composition (Mg—Ca0.8) was obtained. After the alloy settled for ½ hour, it was cast into ingots. The ingots were dry turned to 38 millimeter diameter round bars and sectioned with a $SiO_2$ abrasive cutting wheel into 12.7 millimeter thick samples. The face of each sample was machined by polycrystalline diamond (PCD) insets utilizing the set-up shown in FIG. 2. The surface cutting speed, feed, and depth-of-cut were 2400 meters per minute, 0.05 millimeters per revolution, and 0.2 millimeters, respectively. Burnishing was performed using an Ecoroll HG13 tool. It uses a ceramic ball made of silicon nitride that is 12.7 millimeters in diameter and has 10 millimeters of free stroke to accommodate for elevation changes. The ceramic ball sits on a pressurized hydro cushion via a high pressure hydraulic unit. This avoids the contact between ball and spherical housing and guarantees free rolling along the sample surface. The hydraulic unit is capable of hydraulic pressures up to 40 megapascals. The power carrying fluid is anti-wear, dual purpose Aries 15 oil functioning as both coolant and lubricant. Samples were burnished at hydraulic pressures of 2, 4, 6, 8, and 10 megapascals. Feeds varied from 0.04 to 0.2 millimeters. Speed varied from 50 to 890 millimeters per minute.

The surface roughness was measured using a Veeco DekTak IIA Profilometer. Microhardness was measured using a Buehler Hardness Tester with a Knoop indenter. The applied forces were 10 $g_f$. The residual stress was measured using a 4-axis Bruker D8 XRD by applying 35 milli-Amps current and 40 kilo-volts using a copper source. The wavelength was 0.1542 nanometers. The collimator was 0.8 millimeters in diameter. Assuming plane stress conditions, residual stresses were calculated based $sin^2\psi$ method at a 2θ=118.48°.

The resultant surface integrity from hybrid dry cutting/hydrostatic burnishing with the previously mentioned process parameters are presented below. The effect on the degradation rate was measured by an immersion test. In an immersion test, the evolved hydrogen is collected over time and then using the stoichiometry of the degradation reaction, degradation rate is calculated. The corresponding degradation rates are provided in FIGS. 4-6. The added burnishing treatment after dry cutting proved to decrease the degradation rate of the biodegradable medical device. Also, increasing the hydraulic pressure proved to decrease the corrosion rate further.

What is claimed is:

1. A non-peened biodegradable medical device with custom degradation kinetics and topography comprising:
   a non-peened biodegradable material having a density of from 1.5 g/cm³ to 3.5 g/cm³ and made from a biodegradable implant material and an alloying element;
   wherein the biodegradable implant material includes magnesium;
   wherein the alloying element includes calcium and is present in an amount of 0.8 percent by weight; and wherein the biodegradable medical device has a degradation rate of from 0.001 millimeters per year to 20 millimeters per year in an environment having a pH of 7.5 or less;

wherein the biodegradable medical device has a maximum residual stress on or below a surface of from −170 megapascals to −20 megapascals;

wherein the biodegradable medical device has a maximum hardness on or below the surface of from 40 HV to 140 HV;

wherein the biodegradable medical device has a grain size of from 100 micrometers to 700 micrometers; and wherein the biodegradable medical device has a surface roughness of from 0.1 micrometers to 10 micrometers.

2. The biodegradable medical device according to claim 1, wherein the biodegradable medical device has a degradation rate of from 0.1 millimeters per year to 1 millimeter per year.

3. The biodegradable medical device according to claim 1, wherein the biodegradable medical device has a maximum residual stress on or below the surface of from −150 megapascals to −100 megapascals.

4. The biodegradable medical device according to claim 1, wherein the biodegradable medical device has a maximum residual stress depth of from 50 micrometers to 300 micrometers.

5. The biodegradable medical device according to claim 1, wherein the biodegradable medical device has a residual stress on a top surface of from −100 megapascals to −50 megapascals.

6. The biodegradable medical device according to claim 1, wherein the biodegradable medical device has a residual stress on a top surface of from −90 megapascals to −60 megapascals.

7. The biodegradable medical device according to claim 1, wherein the biodegradable medical device has a maximum hardness on or below the surface of from 40 HV to 75 HV.

8. The biodegradable medical device according to claim 1, wherein the biodegradable medical device has a maximum hardness depth of from 5 micrometers to 175 micrometers.

9. The biodegradable medical device according to claim 1, wherein the biodegradable medical device has a maximum hardness depth of from 25 micrometers to 100 micrometers.

10. The biodegradable medical device according to claim 1, wherein the biodegradable medical device has a maximum hardness on a top surface of from 50 HV to 100 HV.

11. The biodegradable medical device according to claim 1, wherein the biodegradable medical device has a maximum hardness on a subsurface of from 40 to 50 HV.

12. The biodegradable medical device according to claim 1, wherein the biodegradable medical device has a surface roughness of from 0.1 to 8 micrometers.

13. The biodegradable medical device according to claim 1, wherein the biodegradable medical device has a grain size of from 100 micrometers to 300 micrometers.

14. The biodegradable medical device according to claim 1, wherein the biodegradable material has a density of from 1.7 g/cm$^3$ to 2.0 g/cm$^3$.

15. The biodegradable medical device according to claim 1, wherein the biodegradable medical device is an implant or a bone substitute.

16. The biodegradable medical device according to claim 1, wherein the biodegradable medical device is chosen from the group consisting of a bone screw, a rod, or a plate.

17. The biodegradable medical device according to claim 1, produced by a process of hybrid dry cutting/hydrostatic burnishing.

* * * * *